US006764852B2

(12) United States Patent
Cornelis et al.

(10) Patent No.: US 6,764,852 B2
(45) Date of Patent: Jul. 20, 2004

(54) INTERNAL RIBOSOME ENTRY SITE, VECTOR CONTAINING SAME AND USES THEREOF

(75) Inventors: Sigrid Cornelis, Gent (BE); Rudi Beyaert, Zingem (BE)

(73) Assignee: Vlaams Interuniversitair Instituut Voor Biotechnologie VZW, Zwijnaarde (BE)

( * ) Notice: Subject to any disclaimer, the term of this patent is extended or adjusted under 35 U.S.C. 154(b) by 0 days.

(21) Appl. No.: 09/915,060

(22) Filed: Jul. 25, 2001

(65) Prior Publication Data

US 2002/0049181 A1 Apr. 25, 2002

Related U.S. Application Data

(63) Continuation of application No. PCT/EP00/00643, filed on Jan. 26, 2000.

(51) Int. Cl.[7] ...................... C12M 15/85; C12M 15/63; C07H 21/04; A61K 48/00
(52) U.S. Cl. ..................... 435/325; 536/23.1; 536/24.1; 514/44; 435/320.1
(58) Field of Search ............................... 536/23.1, 24.1; 514/44; 435/320.1, 325

(56) References Cited

FOREIGN PATENT DOCUMENTS

WO      WO 98/21321      5/1998

OTHER PUBLICATIONS

Xiang et.al.; Molecular Cloning and Expression of Alternatively Spliced PITSLRE Protein Kinase Isoforms, 1994, Journal of Biological Chemistry, vol. 269: 15786–15794.*
Parsels et.al.; The Role for Translational Control of the Cell Cycle, 1998, Cancer Journal from Scientific American, vol. 4,No. 5: 287–295.*
Gururajan et al., Duplication of a genomic region containing the Cdc2L1–2 and MMP21–22 genes on human chromosome 1p36.3 and their linkage to D1Z2, Genome Research, vol. 8, pp. 929–939.*
Parsels et al., "The Role for Translational Control of the Cell Cycle", *Cancer Journal*, vol. 4, No. 5, pp. 287–295, Sep. 1998.

Xiang et al., "Molecular Cloning and Expression of Alternatively Spliced PITSLRE Protein Kinase Isoforms", *The Journal of Biological Chemistry*, vol. 269, No. 22, pp. 15786–15794, Jun. 3, 1994.
PCT International Preliminary Examination Report, PCT/EP00/00643, dated Mar. 6, 2001, 8 pages.
PCT International Search Report, PCT/EP00/00643, dated Jun. 28, 2000, 9 pages.
Written Opinion, PCT/EP00/00643, dated Nov. 7, 2000, 8 pages.
Bag et al., "Cell Cycle Regulated Translation of mRNA in Rat Muscle Cells", ENDFIELD *Federation Proceedings*, Abstract XP–002110262.
Cornelis et al., "Identification and Characterization of a Novel Cell Cycle–Regulated Internal Ribosome Entry Site", *Molecular Cell*, vol. 5, pp. 597–605, Apr. 2000.
Fussenegger et al., "Regulated multicistronic expression technology for mammalian metabolic engineering", *Cytotechnology*, vol. 28, pp. 111–125, 1998.
Gururajan et al., "Duplication of a Genomic Region Containing the Cdc2L1–2 and MMP21–22 Genes on Human Chromosome 1p36.3 and their Linkage to D1Z2", *Genome Research*, vol. 8, pp. 929–939, Sep. 1998.
Havenga et al., "Second gene expression in bicistronic constructs using short synthetic intercistrons and viral IRES sequences", *Molecular Immunology*, vol. 222, No. 2, pp. 319–327, 1998.
Hengst et al., "Translational Control of p27[Kip1] Accumulation During the Cell Cycle", *Science*, vol. 271, pp. 1861–1864, Mar. 29, 1996.

* cited by examiner

*Primary Examiner*—David Guzo
*Assistant Examiner*—Daniel M. Sullivan
(74) *Attorney, Agent, or Firm*—TraskBritt

(57) ABSTRACT

Two isoforms, p110 and p58 of PITSLRE protein kinase, can be translated from the same p110 (a2-2) mRNA by an internal ribosome entry process. Accordingly, p110 and p58, two proteins with punitive functions, are translated from a single mRNA species by using two AUGs within the same reading frame. These two proteins share the 439 C-terminal amino acids that contain the kinase domain. The internal ribosomal entry site ("IRES") in the polycistronic p110 mRNA is the first IRES completely localized in the coding region of a cellular mRNA. Moreover, it was unexpectedly found that the IRES element is cell cycle regulated. Translation of p58 occurs in the G2/M stage of the cycle.

23 Claims, 6 Drawing Sheets

SEQUENCE LISTING

```
<160> NUMBER OF SEQ ID NOS: 45

<210> SEQ ID NO 1
<211> LENGTH: 222
<212> TYPE: DNA
<213> ORGANISM: Homo sapiens

<400> SEQUENCE: 1
gacatcagcg acagcgagag gaagaccagc tcggccgagt cctcgtcagc agaatcaggc      60
tcaggttctg aggaagaaga ggaggaggag gaagaggagg aggaggaagg gagcaccagt     120
gaagaatcag aggaggaaga ggaagaggag gaggaggaga ccggcagcaa ctctgaggag     180
gcatcagagc agtctgccga agaagtaagt gaggaagaaa tg                        222

<210> SEQ ID NO 2
<211> LENGTH: 222
<212> TYPE: RNA
<213> ORGANISM: Homo sapiens

<400> SEQUENCE: 2
gacaucagcg acagcgagag gaagaccagc ucggccgagu ccucgucagc agaaucaggc      60
ucagguucug aggaagaaga ggaggaggag gaagaggagg aggaggaagg gagcaccagu     120
gaagaaucag aggaggaaga ggaagaggag gaggaggaga ccggcagcaa cucugaggag     180
gcaucagagc agucugccga agaaguaagu gaggaagaaa ug                        222

<210> SEQ ID NO 3
```

```
<211> LENGTH: 2471
<212> TYPE: DNA
<213> ORGANISM: Homo sapiens

<400> SEQUENCE: 3
atacaggaag tgacgatact tttggcgcgc gcggttgctg tttcttctct ggctccggga      60
ccggcggcgg cggcggcggc acgggcggcg gcgtagggtg ttttaactca aatgggtgat     120
gaaaaggact cttggaaagt gaaaacttta gatgaaattc ttcaggaaaa gaaacgaagg     180
aaggaacaag aggagaaagc agagataaaa cgcttaaaaa attctgatga ccgggattcc     240
aagcgggatt cccttgagga gggggagctg agagatcact gcatggagat cacaataagg     300
aactccccgt atagaagaga agactctatg gaagacagag gagaagaaga tgattctttg     360
gccatcaaac caccccagca aatgtctcgg aaagaaaaag ttcatcacag aaaagatgaa     420
aagagaaaag agaaaaagca tgctagagtg aagaagaaag aaagagagca cgaacgtcgg     480
aaacgacatc gagaagaaca ggataaagct cgccgggaat gggaaagaca gaagagaagg     540
gaaatggcaa gggagcattc caggagagaa aggggaatg atggcgtgtg cctcttcagg     600
gaccgcttgg agcagttaga aaggaagcgg gagcgggagc gcaagatgcg ggagcagcag     660
aaggagcagc gggagcagaa ggagcgcgag cggcgggcgg aggagcggcg caaggagcgg     720
gaggcccgca gggaagtgtc tgcacatcac cgaacgatga gagaggacta cagcgacaaa     780
gtgaaagcca gccactggag tcgcagcccg cctcggccgc cgcgggagcg gttcgagttg     840
ggagacggcc ggaagccagt aaaagaagag aaaatggaag aaagggacct gctgtccgac     900
ttacaggaca tcagcgacag cgagaggaag accagctcgg ccgagtcctc gtcagcagaa     960
tcaggctcag gttctgagga agaagaggag gaggaggaag aggaggagga ggaagggagc    1020
accagtgaag aatcagagga ggaagaggaa gaggaggagg aggaccgg cagcaactct    1080 gaggaggcat cagagcagtc tgccgaagaa gtaagtgagg aagaaatgag tgaagatgaa    1140
gaacgagaaa atgaaaacca cctcttggtt gttccagagt cacggttcga ccgagattcc    1200
ggggagagtg aagaagcaga ggaagaagtg ggtgagggaa cgccgcagag cagcgccctg    1260
acagagggcg actatgtgcc cgactcccct gccctgtcgc ccatcgagct caagcaggag    1320
ctgcccaagt acctgccggc cctgcagggc tgccggagcg tcgaggagtt ccagtgcctg    1380
aacaggatcg aggagggcac ctatggagtg gtctacagag caaaagacaa gaaaacagat    1440
gaaattgtgg ctctaaagcg gctgaagatg gagaaggaga aggagggctt cccgatcacg    1500
tcgctgaggg agatcaacac catcctcaag gcccagcatc caacatcgt caccgttaga    1560 gagattgtgg tgggcagcaa catggacaag atctacatcg tgatgaacta tgtggagcac    1620
gacctcaaga gcctgatgga gaccatgaaa cagcccttcc tgccagggga ggtgaagacc    1680
ctgatgatcc agctgctgcg tgggtgaaa cacctgcacg acaactggat cctgcaccgt    1740
gacctcaaga cgtccaacct gctgctgagc cacgccggca tcctcaaggt gggtgacttc    1800
gggctggcgc gggagtacgg atcccctctg aaggcctaca ccccggtcgt ggtgaccctg    1860
tggtaccgcg cccagagct gctgcttggt gccaaggaat actccacggc cgtggacatg    1920
tggtcagtgg gttgcatctt cggggagctg ctgactcaga agcctctgtt ccccgggaag    1980
tcagaaatcg atcagatcaa caaggtgttc aaggatctgg gaccccag tgagaaaatc    2040 tggcccggct acagcgagct cccagcagtc aagaagatga ccttcagcag acacccctac    2100
aacaacctcc gcaagcgctt cggggctctg ctctcagacc agggcttcga cctcatgaac    2160
aagttcctga cctacttccc cgggaggagg atcagcgctg aggacggcct caagcatgag    2220
```

| tatttccgcg agacccccct cccatcgac ccctccatgt tccccacgtg gcccgccaag | 2280 |
| agcgagcagc agcgtgtgaa gcggggcacc agcccgaggc ccctgaggg aggcctgggc | 2340 |
| tacagccagc tgggtgacga cgacctgaag gagacgggct tccaccttac caccacgaac | 2400 |
| caggggggcct ctgccgcggg ccccggcttc agcctcaagt tctgaaggtc agagtggacc | 2460 |
| ccgtcatggg g | 2471 |

<210> SEQ ID NO 4
<211> LENGTH: 30
<212> TYPE: DNA
<213> ORGANISM: Homo sapiens

<400> SEQUENCE: 4

| gacatcagcg acagcgagag gaagaccagc | 30 |

<210> SEQ ID NO 5
<211> LENGTH: 468
<212> TYPE: DNA
<213> ORGANISM: Homo sapiens

<400> SEQUENCE: 5

| cacgaacgtc ggaaacgaca tcgagaagaa caggataaag ctcgccggga atgggaaaga | 60 |
| cagaagagaa gggaaatggc aagggagcat tccaggagag aaaggggaa tgatggcgtg | 120 |
| tgcctcttca gggaccgctt ggagcagtta gaaaggaagc gggagcggga gcgcaagatg | 180 |
| cgggagcagc agaaggagca gcgggagcag aaggagcgcg agcggcgggc ggaggagcgg | 240 |
| cgcaaggagc gggaggcccg cagggaagtg tctgcacatc accgaacgat gagagaggac | 300 |
| tacagcgaca aagtgaaagc cagccactgg agtcgcagcc cgcctcggcc gccgcgggag | 360 |
| cggttcgagt tgggagacgg ccggaagcca gtaaaagaag agaaaatgga agaaagggac | 420 |
| ctgctgtccg acttacagga catcagcgac agcgagagga agaccagc | 468 |

<210> SEQ ID NO 6
<211> LENGTH: 660
<212> TYPE: DNA
<213> ORGANISM: Homo sapiens

<400> SEQUENCE: 6

| cacgaacgtc ggaaacgaca tcgagaagaa caggataaag ctcgccggga atgggaaaga | 60 |
| cagaagagaa gggaaatggc aagggagcat tccaggagag aaaggggaa tgatggcgtg | 120 |
| tgcctcttca gggaccgctt ggagcagtta gaaaggaagc gggagcggga gcgcaagatg | 180 |
| cgggagcagc agaaggagca gcgggagcag aaggagcgcg agcggcgggc ggaggagcgg | 240 |
| cgcaaggagc gggaggcccg cagggaagtg tctgcacatc accgaacgat gagagaggac | 300 |
| tacagcgaca aagtgaaagc cagccactgg agtcgcagcc cgcctcggcc gccgcgggag | 360 |
| cggttcgagt tgggagacgg ccggaagcca gtaaaagaag agaaaatgga agaaagggac | 420 |
| ctgctgtccg acttacagga catcagcgac agcgagagga agaccagctc ggccgagtcc | 480 |
| tcgtcagcag aatcaggctc aggttctgag gaagaagagg aggaggagga agaggaggag | 540 |
| gaggaaggga gcaccagtga agaatcagag gaggaagagg aagaggagga ggaggagacc | 600 |
| ggcagcaact ctgaggaggc atcagagcag tctgccgaag aagtaagtga ggaagaaatg | 660 |

<210> SEQ ID NO 7
<211> LENGTH: 87
<212> TYPE: DNA

-continued

<213> ORGANISM: Homo sapiens

<400> SEQUENCE: 7
gaagaagagg aggaggagga agaggaggag gaggaaggga gcaccagtga agaatcagag    60
gaggaagagg aagaggagga ggaggag                                        87

<210> SEQ ID NO 8
<211> LENGTH: 30
<212> TYPE: DNA
<213> ORGANISM: Artificial Sequence
<220> FEATURE:
<221> NAME/KEY: misc_feature
<223> OTHER INFORMATION: Artificial Sequence: mutation primer in frame
      NotI

<400> SEQUENCE: 8
agcctcaagt tcgcggccgc agagtggacc                                     30

<210> SEQ ID NO 9
<211> LENGTH: 21
<212> TYPE: DNA
<213> ORGANISM: Artificial Sequence
<220> FEATURE:
<221> NAME/KEY: misc_feature
<223> OTHER INFORMATION: Artificial Sequence: primer

<400> SEQUENCE: 9
gaggaagaag cgagtgaaga t                                              21

<210> SEQ ID NO 10
<211> LENGTH: 22
<212> TYPE: DNA
<213> ORGANISM: Artificial Sequence
<220> FEATURE:
<221> NAME/KEY: misc_feature
<223> OTHER INFORMATION: Artificial Sequence: primer

<400> SEQUENCE: 10
gacagcgaga aagaccagct cg                                             22

<210> SEQ ID NO 11
<211> LENGTH: 35
<212> TYPE: DNA
<213> ORGANISM: Artificial Sequence
<220> FEATURE:
<221> NAME/KEY: misc_feature
<223> OTHER INFORMATION: Artificial Sequence:  5'-end primer

<400> SEQUENCE: 11
ctagtctaga aaagtgaaaa ctttagatga aattc                               35

<210> SEQ ID NO 12
<211> LENGTH: 35
<212> TYPE: DNA
<213> ORGANISM: Artificial Sequence
<220> FEATURE:
<221> NAME/KEY: misc_feature
<223> OTHER INFORMATION: Artificial Sequence:  3'-end primer

<400> SEQUENCE: 12
tgcatgccat ggatgtcgtt tccgacgttc gtgcg                               35

<210> SEQ ID NO 13
<211> LENGTH: 35
<212> TYPE: DNA
<213> ORGANISM: Artificial Sequence

```
<220> FEATURE:
<221> NAME/KEY: misc_feature
<223> OTHER INFORMATION: Artificial Sequence: 3'-end primer

<400> SEQUENCE: 13
tgcatgccat ggtcctctct catcgttcgg tgatg                          35

<210> SEQ ID NO 14
<211> LENGTH: 35
<212> TYPE: DNA
<213> ORGANISM: Artificial Sequence
<220> FEATURE:
<221> NAME/KEY: misc_feature
<223> OTHER INFORMATION: Artificial Sequence: 3'-end primer

<400> SEQUENCE: 14
catgccatgg tcttcctctc gctgtcgctg atgtc                          35

<210> SEQ ID NO 15
<211> LENGTH: 32
<212> TYPE: DNA
<213> ORGANISM: Artificial Sequence
<220> FEATURE:
<221> NAME/KEY: misc_feature
<223> OTHER INFORMATION: Artificial Sequence: 5'-end primer

<400> SEQUENCE: 15
ctagtctaga catcaccgaa cgatgagaga gg                             32

<210> SEQ ID NO 16
<211> LENGTH: 26
<212> TYPE: DNA
<213> ORGANISM: Artificial Sequence
<220> FEATURE:
<221> NAME/KEY: misc_feature
<223> OTHER INFORMATION: Artificial Sequence: hairpin forming double-
      stranded oligonucleotide

<400> SEQUENCE: 16
cgcgtggcga gattttcagg agtcac                                    26

<210> SEQ ID NO 17
<211> LENGTH: 26
<212> TYPE: DNA
<213> ORGANISM: Artificial Sequence
<220> FEATURE:
<221> NAME/KEY: misc_feature
<223> OTHER INFORMATION: Artificial Sequence: hairpin forming double-
      stranded oligonucleotide

<400> SEQUENCE: 17
tcgagtgact cctgaaaatc tcgcca                                    26

<210> SEQ ID NO 18
<211> LENGTH: 40
<212> TYPE: DNA
<213> ORGANISM: Artificial Sequence
<220> FEATURE:
<221> NAME/KEY: misc_feature
<223> OTHER INFORMATION: Artificial Sequence: E-tag probe

<400> SEQUENCE: 18
acgcggttcc agcggatccg gatacggctc cggcgcacct                     40

<210> SEQ ID NO 19
<211> LENGTH: 8
<212> TYPE: RNA
```

```
<213> ORGANISM: Artificial Sequence
<220> FEATURE:
<221> NAME/KEY: misc_feature
<223> OTHER INFORMATION: Artificial Sequence: primer

<400> SEQUENCE: 19 crccaugg                                                              8

<210> SEQ ID NO 20
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 20 cucaaaugg                                                             9

<210> SEQ ID NO 21
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 21 gggugauga                                                             9

<210> SEQ ID NO 22
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 22 uuuagauga                                                             9

<210> SEQ ID NO 23
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 23 uucugauga                                                             9

<210> SEQ ID NO 24
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 24 acugcaugg                                                             9

<210> SEQ ID NO 25
<211> LENGTH: 9
<212> TYPE: RNA
<213> ORGANISM: Artificial Sequence
```

```
<220> FEATURE:
<221> NAME/KEY: misc_feature
<223> OTHER INFORMATION: Artificial Sequence: primer

<400> SEQUENCE: 25 acucuaugg                                                                  9

<210> SEQ ID NO 26
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 26 agaagauga                                                                  9

<210> SEQ ID NO 27
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 27 agcaaaugu                                                                  9

<210> SEQ ID NO 28
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 28 aaaagauga                                                                  9

<210> SEQ ID NO 29
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 29 aaagcaugc                                                                  9

<210> SEQ ID NO 30
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 30 cgggaaugg                                                                  9

<210> SEQ ID NO 31
<211> LENGTH: 9
<212> TYPE: RNA
<213> ORGANISM: Artificial Sequence
<220> FEATURE:
```

```
<221> NAME/KEY: misc_feature
<223> OTHER INFORMATION: Artificial Sequence: primer

<400> SEQUENCE: 31 gggaaaugg                                                                         9

<210> SEQ ID NO 32
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 32 ggggaauga                                                                         9

<210> SEQ ID NO 33
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 33 gaugaugg                                                                          9

<210> SEQ ID NO 34
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 34 gcaagaugc                                                                         9

<210> SEQ ID NO 35
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 35 gaacgauga                                                                         9

<210> SEQ ID NO 36
<211> LENGTH: 9
<212> TYPE: RNA
<213> ORGANISM: Artificial Sequence
<220> FEATURE:
<221> NAME/KEY: misc_feature
<223> OTHER INFORMATION: Artificial Sequence: primer

<400> SEQUENCE: 36 agaaaugg                                                                          9

<210> SEQ ID NO 37
<211> LENGTH: 9
<212> TYPE: RNA
<213> ORGANISM: Artificial Sequence
<220> FEATURE:
<221> NAME/KEY: misc_feature
```

```
<223> OTHER INFORMATION: Artificial Sequence: primer

<400> SEQUENCE: 37 aagaaauga                                                              9

<210> SEQ ID NO 38
<211> LENGTH: 36
<212> TYPE: DNA
<213> ORGANISM: Artificial Sequence
<220> FEATURE:
<221> NAME/KEY: misc_feature
<223> OTHER INFORMATION: Artificial Sequence: 5'-end primer

<400> SEQUENCE: 38
tgaccggaat tcatgggtga tgaaaggac tcttgg                                36

<210> SEQ ID NO 39
<211> LENGTH: 39
<212> TYPE: DNA
<213> ORGANISM: Artificial Sequence
<220> FEATURE:
<221> NAME/KEY: misc_feature
<223> OTHER INFORMATION: Artificial Sequence: 3'-end primer

<400> SEQUENCE: 39
tgaccggaat tctgaccttc agaacttgag gctgaagcc                            39

<210> SEQ ID NO 40
<211> LENGTH: 33
<212> TYPE: DNA
<213> ORGANISM: Artificial Sequence
<220> FEATURE:
<221> NAME/KEY: misc_feature
<223> OTHER INFORMATION: Artificial Sequence:  3'-end primer

<400> SEQUENCE: 40
ttcttcatct tcacccatgg cttcctcact tac                                  33

<210> SEQ ID NO 41
<211> LENGTH: 31
<212> TYPE: DNA
<213> ORGANISM: Artificial Sequence
<220> FEATURE:
<221> NAME/KEY: misc_feature
<223> OTHER INFORMATION: Artificial Sequence: 5'-end primer

<400> SEQUENCE: 41
ctagtctaga gcacgaacgt cggaaacgac a                                    31

<210> SEQ ID NO 42
<211> LENGTH: 40
<212> TYPE: DNA
<213> ORGANISM: Artificial Sequence
<220> FEATURE:
<221> NAME/KEY: misc_feature
<223> OTHER INFORMATION: Artificial Sequence:  5'-end primer

<400> SEQUENCE: 42
ctagtctaga gacatcagcg acagcgagag gaagaccagc                           40

<210> SEQ ID NO 43
<211> LENGTH: 35
<212> TYPE: DNA
<213> ORGANISM: Artificial Sequence
<220> FEATURE:
<221> NAME/KEY: misc_feature
<223> OTHER INFORMATION: Artificial Sequence:  primer
```

```
<400> SEQUENCE: 43
ccatcgatag aacctgagcc tgattctgct gacga                                    35

<210> SEQ ID NO 44
<211> LENGTH: 34
<212> TYPE: DNA
<213> ORGANISM: Artificial Sequence
<220> FEATURE:
<221> NAME/KEY: misc_feature
<223> OTHER INFORMATION: Artificial Sequence:  primer

<400> SEQUENCE: 44
ccatcgatac cggcagcaac tctgaggagg catc                                     34

<210> SEQ ID NO 45
<211> LENGTH: 33
<212> TYPE: DNA
<213> ORGANISM: Artificial Sequence
<220> FEATURE:
<221> NAME/KEY: misc_feature
<223> OTHER INFORMATION: Artificial Sequence:  primer

<400> SEQUENCE: 45
ttcttcatct tcacccatgg cttcctcact tac                                      33
```

INTERNAL RIBOSOME ENTRY SITE, VECTOR CONTAINING SAME AND USES THEREOF

CROSS-REFERENCE TO RELATED APPLICATIONS

This application is a continuation of pending PCT International Application No. PCT/EP00/00643 (International Publication No. WO 00/44896, International filing date Jan. 26, 2000, designating the United States of America), the contents of the entirety of said publication being incorporated herein by this reference.

TECHNICAL FIELD

The invention relates to an isolated and/or recombinant nucleic acid molecule, preferably a cloned DNA sequence element that can be incorporated into expression vectors for improving translation of a given mRNA. The invention enables the translation of mRNA in a cap-dependent and in a cap-independent manner in eukaryotic cells. The DNA sequence element comprises the so-called internal ribosomal entry site ("IRES").

BACKGROUND

The PITSLRE protein kinase family is a large supergene family related to the master mitotic protein kinase, p34cdc2. PITSLRE protein kinases are encoded by the duplicated genes cell division cycle 2-like 1 (Cdc2L1) and Cdc2L2, which span approximately 140 kb on human chromosome 1p36.3 (Gururajan et al., 1998). These genes express almost identical protein kinases of 110 kDa, which contain at their C-terminal end the open reading frame of a smaller isoform of 58 kDa: $p58^{PITSLRE}$. At present, the function of PITSLRE kinases remains elusive. The reason for the high number of different isoforms is also not clear. Only the p110 and p90 isoforms contain a 30-amino acid region comprised primarily of glutamic acid (83%) (Xiang et al., 1994). Shorter glutamic acid sequences can be found in all isoforms immediately following the first translational start site for the b1 isoform. Several highly basic regions, which could function as bipartite nuclear localization sequences, are found only in the p110 isoforms (Xiang et al., 1994).

The yeast two-hybrid system revealed a direct interaction between the RNA-binding protein, hRNPS1, and the p110 isoforms but not with the smaller isoforms (Loyer et al., 1998).

The wide variation in the expression patterns of the different isoforms and their levels of expression points to isoform-specific functions. While p110 isoforms are ubiquitously expressed in asynchronous cell populations, overexpression of p58 in eukaryotic cells leads to a late mitotic delay due to an apparent failure of cytokinesis. The cells are sequestered at late telophase for an extended period of time (Bunnell et al., 1990). The rate of cell growth in these cells is greatly diminished. Conversely, diminished p58 mRNA levels in CHO fibroblasts are associated with enhanced cell growth, as measured by increased rates of DNA replication (Meyerson et al., 1992). These observations suggest that p58 might participate in normal regulation of the cell cycle or cell death. Additionally, the chromosome region 1p36.3 is often deleted in neuroblastoma and many other tumors. Deletion of this chromosome region occurs late in oncogenesis and is correlated with aggressive tumor growth, suggesting that one or more tumor suppressor genes may reside here (Eipers et al., 1991). Another observation pointing to a role for PITSLRE kinases during cell cycle progression is that during early embryogenesis in Drosophila, when exponential proliferation takes place, the expression level of PITSLRE specific transcripts, encoding the p110 homologue, is maximal. At a later stage when cell proliferation is attenuated, PITSLRE expression drops dramatically (Sauer et al., 1996).

Polycistronic messengers occur frequently in prokaryotic systems. There has been a long-established misunderstanding that the polycistronic messengers did not occur in eukaryotic systems because of the presence of the so-called "cap" at the start of mRNA. Indeed, initiation of translation of the majority of eukaryotic cellular and viral mRNAs results from attachment of ribosomes to the $m^7G$ cap at the 5'-end of the mRNA followed by linear scanning to the initiation codon. However, initiation of translation of a smaller number of eukaryotic mRNAs is 5'-end and cap-independent and, instead, results from direct attachment of ribosomes to an internal ribosomal entry site within the 5' nontranslated region (5' NTR) of the mRNA.

IRES elements were first reported in picornaviral mRNAs which are naturally uncapped but nonetheless efficiently translated (Jang et al., 1988, J. Virol., 62:2636–43). Generally, IRES cannot be identified by sequence homology. Known IRES have been identified and defined functionally (Mountford and Smith, 1995, TIG, 11(5): 179–184). It appears that the conformation of the IRES sequence enables the binding on the ribosome.

It would be useful to identify a sequence element that endows any desired gene with the ability to be efficiently translated and to be translated in a cap-independent manner in particular. Moreover, it would be of great advantage to isolate a sequence element that is cell cycle regulated. Furthermore, it would be extremely useful to have IRES sequence elements with a preferably high translational efficiency to use in expression vectors as well as in gene therapy vectors in order to control mRNA translation and therefore protein synthesis.

SUMMARY OF THE INVENTION

It has been found that two isoforms, p110 and p58 of PITSLRE protein kinase, can be translated from the same PITSLRE by an internal ribosome entry process. This means that p110 and p58, two proteins with putative different functions, are translated from a single mRNA species by using two AUGs within the same reading frame. These two proteins share the 439 C-terminal amino acids that contain the kinase domain. The IRES in the polycistronic PITSLRE is the first IRES completely localized in the coding region of a cellular mRNA. Moreover, it was surprisingly found that the IRES element is cell cycle regulated. Translation of p58 occurs in the G2/M stage of the cell cycle.

BRIEF DESCRIPTION OF THE FIGURES

FIG. 1A illustrates a Western blot analysis with anti-E-tag antibodies of synchronized Ba/F3-$p110^{PITSLRE}$ cells grown in the presence (zVAD$^+$) or absence (zVAD$^-$) of 100 μmolar zVAD-fmk prepared at different time points after IL-3-stimulation. Corresponding cell cycle phases are indicated. FIG. 1 similarly depicts a cell cycle-dependent expression of transfected $p58^{PITSLRE}$. More specifically, the figure demonstrates that the percentage of cells that is in a specific phase of the cell cycle was determined by FACS analysis of the DNA content after staining with propidium iodide (diamond: G1; square: S;

triangle: G2/M). FACS analysis was carried out as follows: Ba/F3 cells were IL-3 depleted for 14 h to arrest cells in G1. DNA content was measured by freezing the cells in the presence of propidium iodide and subsequent FACS analysis. Results are shown for a representative cell clone.

Figure 2:
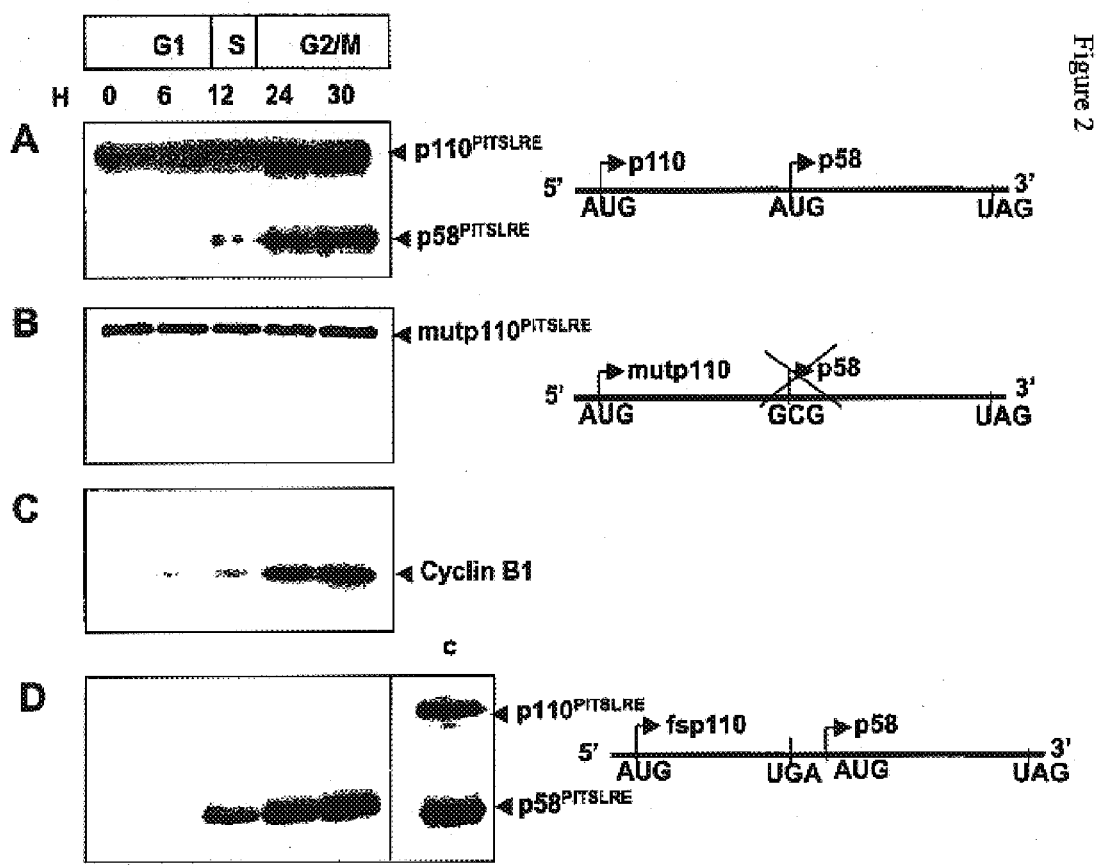

FIG. 2 shows that p58$^{PITSLRE}$ is expressed in G2/M by internal initiation of translation on the full-length p110$^{PITSLRE}$ mRNA. Specifically, Western blot analysis is illustrated with anti-E-tag antibodies (FIGS. 2A, 2B, 2D) or anti-cyclin B1 antibodies (FIG. 2C) of Ba/F3-p110$^{PITSLRE}$ cells (FIG. 2A), Ba/F3-mut-p110$^{PITSLRE}$ cells (FIGS. 2B, 2C) or Ba/F3-fsp-110$^{PITSLRE}$ cells (FIG. 2D) prepared at different time points during cell cycle progression. Cells were synchronized in G1 by IL-3-depletion and released from this G1-block by subsequent stimulation with IL-3 for the times indicated. In (FIG. 2D) "c" is indicating the control experiment with Ba/F3-p110$^{PITSLRE}$, in G2/M phase.

FIGS. 3A and 3B depict the expression of PITSLRE protein kinases during cell cycle progression in Ba/F3 cells. FIG. 3A illustrates Western blot analysis with anti-PITSLRE antibodies, while FIG. 3B illustrates Western blot analysis with anti-cyclin B1 antibodies of Ba/F3 cells. Cells were first synchronized in G1 by IL-3 depletion and released from this G1-block by subsequent stimulation with IL-3 for the times indicated. The corresponding cell cycle phases are indicated. FIG. 3C illustrates Northern blot analysis of total RNA preparations (30 mg) of Ba/F3 cells. The RNA samples were prepared at the same time points as the samples used for Western blot analysis. A PstI restriction fragment (1072 bp) of the mouse p110$^{PITSLRE}$ cDNA was used as a probe. Numbers to the left indicate the length of RNA markers (kb).

Figure 4:
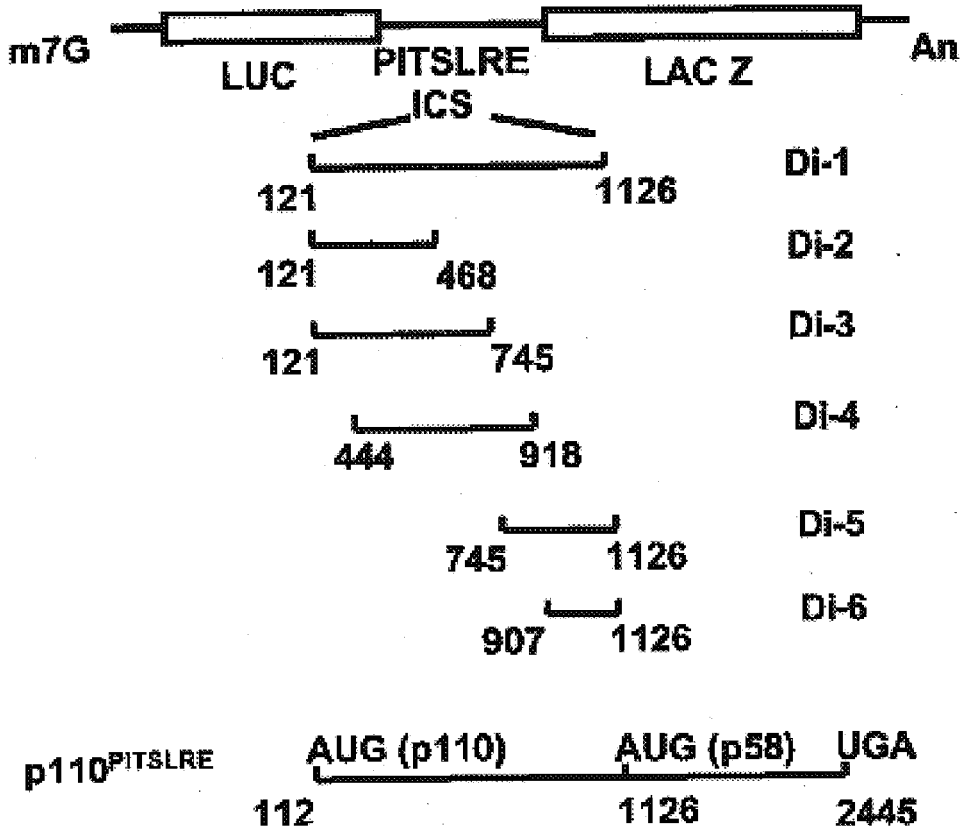
Figure 4:
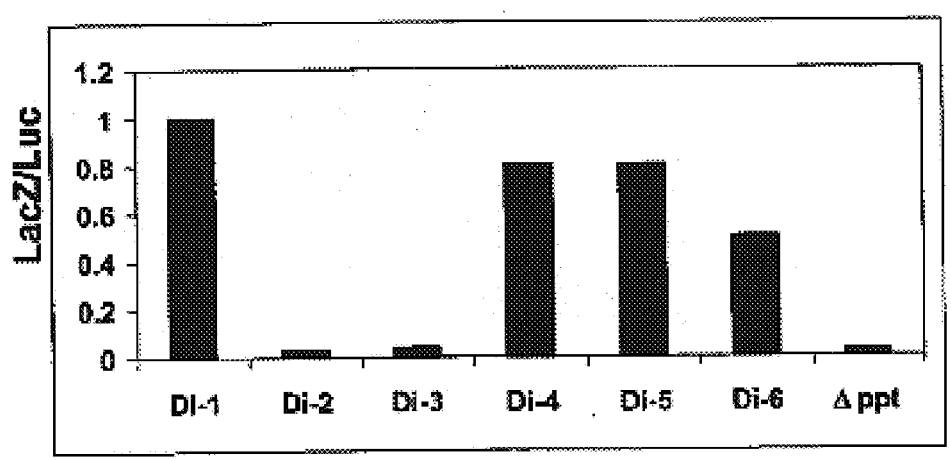
Figure 4:
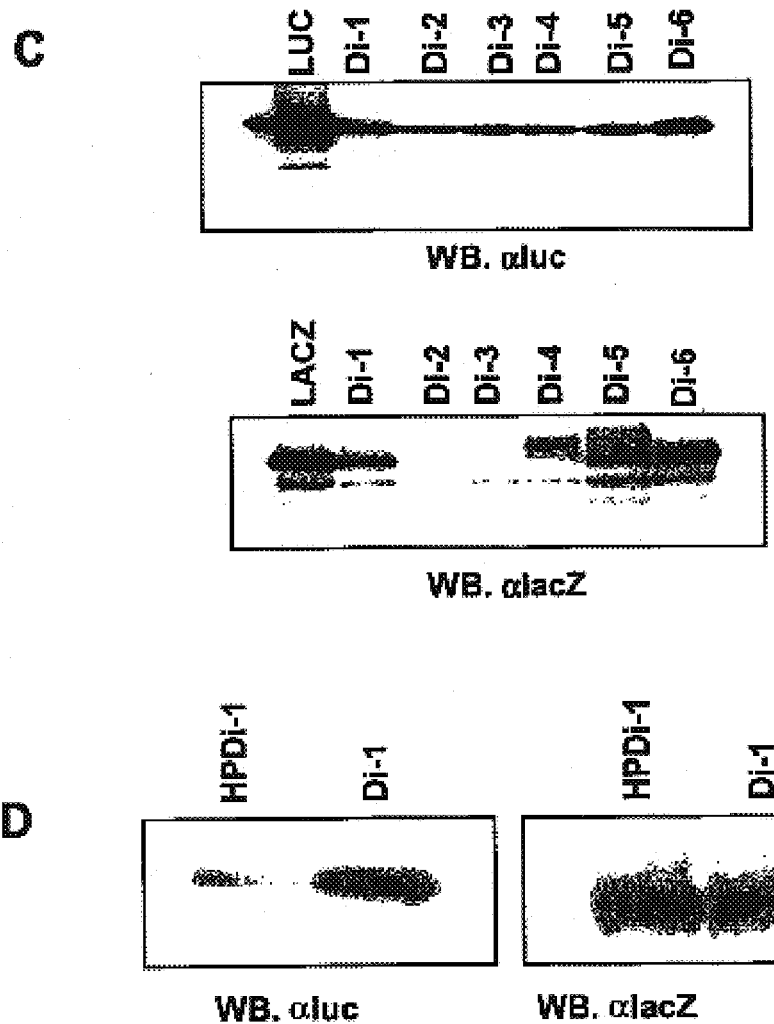
Figure 4:
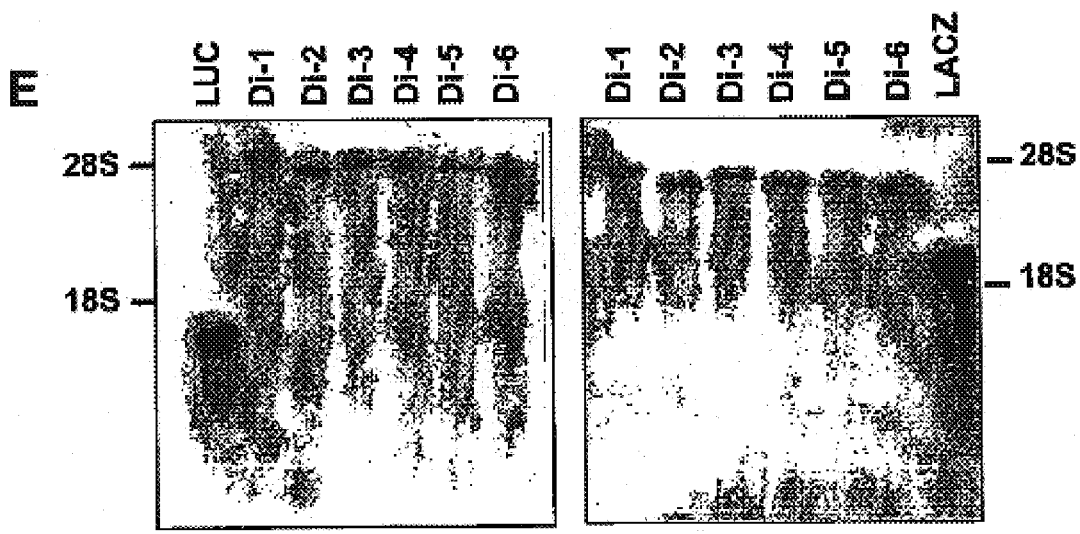

FIG. 4 shows the identification and mapping of an IRES element in the coding region of PITSLRE mRNA. Specifically, FIG. 4A shows the schematic representation of a dicistronic mRNA and of different p110$^{PITSLRE}$-specific sequence elements that were cloned as an ICS between the coding regions for LUC and LACZ. Nucleotide numbers indicate the positions based on the p110$^{PITSLRE}$ cDNA. The dicistronic plasmids (Di-1–Di-6) depicted in FIG. 4A and the dicistronic plasmid Dppt were transiently transfected in 293T cells and expression of LUC and LACZ was analyzed by measurement of their enzymatic activity (bars are representative for four independent transfections) and by Western blot analysis as shown in FIGS. 4B and 4C. In the latter case, 293T cells transfected with pSV-Sport-LUC (LUC) or pSV-Sport-LACZ (LACZ) served as positive control. The upper and the lower panels show detection with anti-luciferase and anti-b-galactosidase antibodies, respectively. FIG. 4D illustrates a comparison of LUC and LACZ expression in 293T cells transiently transfected with Di-1 or HPDi-1 which carries an additional hairpin downstream from the SV40 early promoter. FIG. 4E depicts the Northern blot analysis of dicistronic mRNA expression in 293T cells transfected with the dicistronic constructs indicated on top of each lane (5 mg total RNA/lane), as revealed with LUC-(left) and LACZ-(right) specific probes. Detection of LUC and LACZ induced by overexpression of pSV-Sport-LUC and pSV-Sport-LACZ served as a positive control.

FIGS. 5A and 5B illustrate the upregulation of internal ribosome entry on dicistronic mRNA Di-1 in G2/M-specific Ba/F3 cells. Specifically, Ba/F3 cells were stably transfected with the dicistronic expression plasmid Di-1, and expression of LUC (upper panel) and LACZ (lower panel) was analyzed in two representative nonsynchronized clones. FIG. 5B shows four different Ba/F3-Di-1 clones were synchronized in G1 (open bars) and G2/M (filled bars) by IL-3-depletion (14 h) and restimulation (24 h) with IL-3, respectively. Specific activity of LACZ and LUC was analyzed and expressed as the ratio between LACZ and LUC activities. Data are the mean±s.d. of triplicates.

BEST MODE OF THE INVENTION

The invention relates to the feature that p58 is produced from the PITSLRE mRNA by a mechanism of internal initiation of translation during the G2/M stage of the cell cycle. An embodiment of this invention is disclosed hereafter.

An SV40 early promoter-driven p110$^{PITSLRE}$ isoform (a2-2) fused to an E-tag at its C-terminal end was constructed. This plasmid was stably transfected in the IL-3 dependent pro B-cell line Ba/F3. This system has the advantage that cells can be synchronized in the G1 stage by growth factor depletion. Subsequent stimulation with IL-3 drives the cells simultaneously through further stages of the cell cycle. Via immunoblotting using anti-E-tag, the expression pattern of the transfected PITSLRE construct was studied during cell cycle progression in the Ba/F3-p110$^{PITSLRE}$ transfectants. The p110 isoform was constitutively present during the different stages of the cell cycle. However, only during the G2/M stage was a 58 kDa form co-expressed (FIG. 1A). Cell cycle progression was followed by FACS analysis (FIG. 1B). To make sure that this expression pattern was not a clone-dependent phenomenon, several other clones were analyzed. All displayed a similar pattern.

Also, a minor band of about 100 to 105 kDa was detected. It has been described previously that the p110 isoforms have two potential translational starts near the start of the 5'NTR region. They are separated by 174 bp and they are located in two adjacent exons. A possible mechanism, however, has not been suggested. Perhaps this alternative initiation of translation is a consequence of leaky ribosome scanning. The alternative AUG (at position 283) is located in a more favorable region for initiation of translation compared to the first AUG (position 112) (Table 1).

Figure 1:
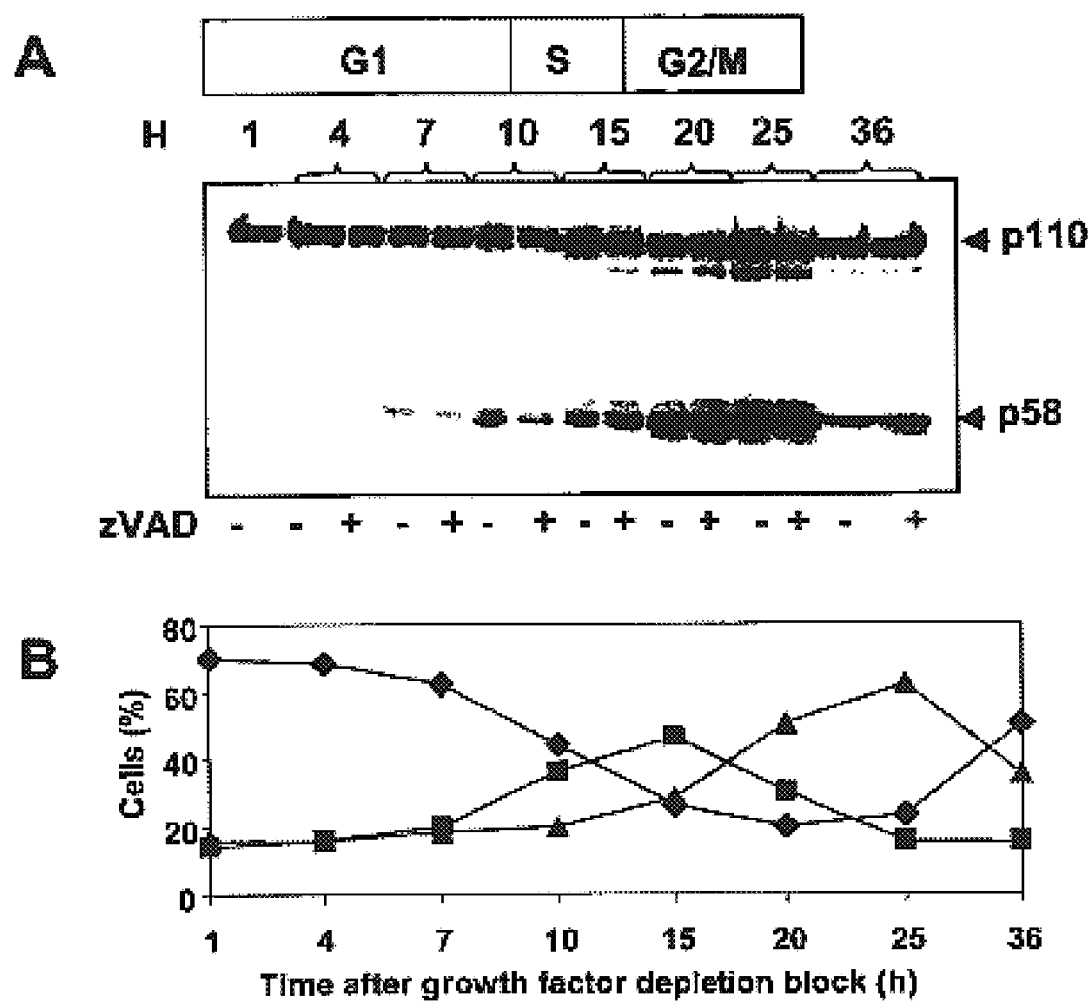
FIG. 1 depicts a cell cycle-dependent expression of transfected $p58^{PITSLRE}$. Specifically.

The origin of the p58 product was initially thought to be the result of a proteolytical process. It has been suggested that glutamic acid regions present in the p110 isoform are potential points of specific proteolytical cleavage. Recently, a possible role for a capase-processed PITSLRE isoform has been suggested by studies of Fas- and TNF-induced cell death. (Lahti et al., 1995, Beyaert et al., 1997, Tang et al., 1998). Transfectants were incubated with the broad spectrum inhibitor of caspases, zVAD.fmk, and the PITSLRE expression pattern was analyzed. As FIG. 1 shows, zVAD-.fmk did not affect G2/M specific expression of p58, excluding the possibility that p58 was generated by proteolytic processing of the p110 isoform by resident caspases.

The p110 isoform contains at its C-terminal end the ORF of isoform p58. Therefore, the G2/M-specific p58 protein was probably translated using the internal AUG as an initiation codon. To verify the latter hypothesis, the internal methionine was mutated to alanine and the mutant cDNA was transfected into the Ba/F3 cell line. Interestingly, when compared with wild type (FIG. 2A), this mutation completely knocked out the p58 expression in the G2/M stage of the cell cycle whereas p110 expression remained unchanged (FIG. 2B)

The expression of cyclin B1 as a marker for the G2/M stage of the cell cycle was used as a control. Cyclin B1 is synthesized during late S, maximally expressed during the G2/M and finally degraded during the anaphase (FIG. 2C).

To rule out the possibility that we mutated a potential proteolytical cleavage site in p110$^{PITSLRE}$ capable of generating a 58 kDa product, we introduced in the p110$^{PITSLRE}$ cDNA a frame shift by deletion of two guanosine nucleotides at positions 926 and 927 upstream of the internal AUG (fsp110$^{PITSLRE}$). This mutation led to a short open reading frame of 867 nucleotides (FIG. 2D). Western blot analysis of stable Ba/F3 transfectants of fsp110$^{PITSLRE}$ revealed that the p58$^{PITSLRE}$ was still produced in G2/M in the absence of p110$^{PITSLRE}$ expression (FIG. 2D). Since expression of the transfected gene was controlled by a constitutive early SV40 promoter, regulation of p58 expression at the transcriptional level was excluded.

Next, it was determined whether p58 and p110 were both derived from one mRNA. It is possible that p58 is translated from another, second messenger derived from the initially transfected cDNA. This second messenger could be produced by cleavage of the transfected messenger by a specific ribonuclease or could be induced by a cryptic promoter element present in the upstream sequence. The exogenous mRNA pattern was followed during cell cycle progression by Northern blot analysis with an E-tag specific probe in the Ba/F3 transfectants. One single messenger of 2.4 kb in all stages of the cell cycle was found at a constant expression level. The 2.4 kb band was absent in nontransfected cells. No additional messenger in the G2/M-specific cell lysates was detected. This shows that the p110 (a2-2) mRNA, encoding p110$^{PITSLRE}$ (a2-2), gives rise to a second PITSLRE protein kinase of 58 kDa.

Figure 3:
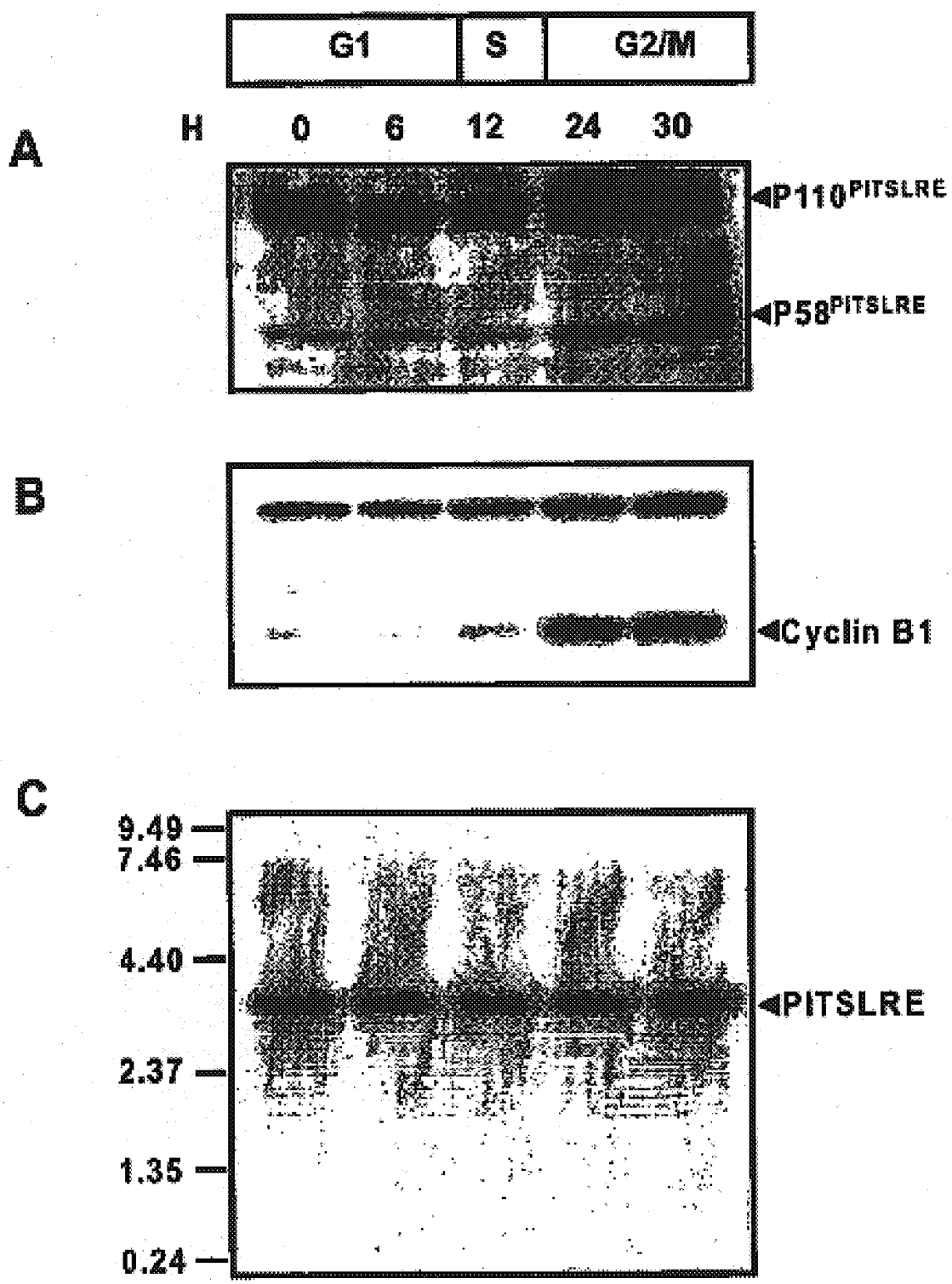

Endogenous PITSLRE protein kinase expression during cell cycle progression was also examined. As shown in FIG. 3, analysis of the Ba/F3 parental cells during cell cycle progression revealed a similar pattern compared to the Ba/F3/p110$^{PITSLRE}$ transfectants. The p110 isoform is permanently present during the different stages of the cell cycle. In accordance with the observations in the transfectants, a strongly enhanced expression of p58 was detected in the G2/M stage.

We further investigated the cell cycle dependence of p58$^{PITSLRE}$ expression by Northern blot analysis using a fragment corresponding to the 3' end of the coding region of mouse p110$^{PITSLRE}$ (Malek and Desiderio, 1994) as a probe. Based on the high conservation in this region between the different human isoforms, we assumed this probe would recognize all murine PITSLRE transcripts. This analysis indicated a single transcript of approximately 3.2 kb in all phases of the cell cycle (FIG. 3C), which is in agreement with previously published observations in mouse tissues (Malek and Desiderio, 1994). No additional G2/M-specific transcript accounting for expression of the 58 kDa product was detectable in Ba/F3 cells, suggesting that G2/M-specific expression of p58$^{PITSLRE}$ was regulated at a post-transcriptional level.

Taken together, the invention thus concerns a nucleotide sequence enabling a cell cycle-dependent initiation of translation of mRNA. More preferably, the sequence is an IRES sequence and, even more preferably, the cell cycle dependency is a G2/M cell cycle dependency. More specifically, the present invention relates to an isolated and/or recombinant nucleic acid molecule, preferably DNA, encoding at least a functional part of a eukaryotic internal ribosomal entry site, which site in the mitotic PITSLRE protein kinase gene comprises the sequence as depicted in SEQ ID NO:1 (of the hereby incorporated SEQUENCE LISTING accompanying this specification) or a functional part thereof. The present invention also concerns a nucleic acid molecule comprising at least a part of the sequence as depicted in SEQ ID NO:1 or a sequence at least substantially homologous thereto.

In another embodiment, the nucleic acid molecule according to the invention relates to at least a part of the sequence as depicted in SEQ ID NO:1 or a sequence which hybridizes under conventional conditions to at least a part of the sequence or its complementary sequence.

Unexpectedly, it has been found that SEQ ID NO:4, being an overlapping sequence of SEQ ID NO:5 and SEQ ID NO:1, has corresponding IRES functionality according to the current invention. Therefore, part of the invention is an isolated and/or recombinant nucleic acid molecule, preferably DNA, comprising at least the sequence as depicted in SEQ ID NO:4, but also an isolated and/or recombinant nucleic acid molecule, preferably DNA, comprising at least the sequence as depicted in SEQ ID NO: 5 and, in addition thereto, an isolated and/or recombinant nucleic acid molecule, preferably DNA, comprising at least the sequence as depicted in SEQ ID NO: 6.

Even more surprisingly, a deletion in the IRES sequence of a sequence with SEQ. ID NO: 7 resulted in a loss of the IRES functionality, indicating that this sequence can play an essential role in IRES functionality. Therefore, part of the invention is an isolated and/or recombinant nucleic acid molecule, preferably DNA, comprising at least the sequence as depicted in SEQ ID NO: 7.

The invention also relates to a chimeric gene comprising the following operably linked polynucleotides:

a) a nucleic acid molecule according to the invention, and b) one or more control sequences.

Part of the present invention is also a vector comprising at least the nucleic acid molecule or comprising the chimeric gene mentioned above and a eukaryotic host cell comprising the nucleic acid molecule or comprising the chimeric gene according to the invention.

The vector can conveniently be an expression vector containing at least a single promoter. A derived expression system comprising a eukaryotic host cell according to the invention forms part of the invention as well.

Another aspect of the invention is a method for cap-independent translation of mRNA by including in an expression vector a translation control element or analogues thereof having the nucleic acid molecule as set forth in SEQ ID NO: 1 and/or SEQ ID NO: 4.

The sequences of the invention can be used to induce a cell cycle-dependent initiation of translation in eukaryotic cells. In particular, the sequences can be used wherein the sequence is a cell cycle-dependent IRES sequence, more preferably a G2/M-dependent IRES sequence.

In addition, the vector or any of the sequences according to the invention can be used for the preparation of a pharmaceutical composition for the treatment and/or prevention of a disease by gene therapy. In this regard, the present invention relates to the use of any recombinant gene endowed with an IRES sequence giving it the ability to be specifically translated in cells that are in the G2/M phase of the cell cycle. The constructs are, therefore, extremely useful in gene therapy approaches that target proliferating cells. In such cases, the IRES drives the translation of an mRNA encoding a protein that is toxic or growth inhibitory for the cells in which it is expressed (e.g., RB, FAS ligand, thyrnidine kinase, caspases; reviewed in Tio et al., 1998), or which restores the expression of proteins that are damaged or missing. The G2/M-specific activity of the IRES results in specific expression of the protein in proliferating cells, leaving the other cells intact. One embodiment of the invention is the use of the IRES in cancer gene therapy by blocking tumor cell growth or inducing tumor cell death.

Additionally, blocking the growth of tumor blood vessels, which are required for the growth of tumors, can be achieved.

Another embodiment of this invention is the use of the IRES in the treatment of restenosis, which results from the abnormal growth of blood vessel smooth muscle cells following angioplasty forcoronary arterydisease and peripheral vascular disease. A vessel-expansion technique called balloon angioplasty is one of the most popular treatments for the cardiovascular blockages that commonly lead to heart attacks. However, due to the mild tissue damage at the surgical site, many patients experience an exaggerated, post-operative healing response, whereby vascular cells proliferate to form a scar that re-clogs the artery. This re-occlusion of the artery is called restenosis and affects up to 50% of the patients receiving primary balloon angioplasty (Schwartz et al., 1992). The effectiveness of adenovirus as a gene therapy vector in animal models of restenosis is well documented (Gerard and Collen, 1997). Therefore, recombinant adenoviral vectors in which the IRES drives the expression of a gene product which affects smooth muscle cell proliferation are constructed in order to inhibit smooth muscle cell proliferation in culture and in pig coronary artery balloon angioplasty model of restenosis. The IRES-mediated gene therapy can be delivered locally in an integrated angioplasty procedure using catheter-based gene delivery (Varenne et al., 1999), or using other methods known to the people skilled in the art.

The invention also relates to the use of IRES sequences to study the role of proteins in mitosis or to screen for novel regulators of cell proliferation. The regulators can be any chemical or biological compound, including simple or complex inorganic molecules, peptides, peptido-mimetics, proteins, antibodies, carbohydrates, nucleic acids orderivatives thereof. A change in expression of the reporter gene indicates a role for the putative regulator in cell cycle regulation. In case the regulator is a protein, peptide, antibody or nucleic acid, it can be expressed in a bicistronic or polycistronic vector that carries the G2/M-specific IRES as an intercistronic sequence in front of the reporter gene cistron.

In order to clarify what is meant in this description by some terms, a further explanation is hereby given:

The terms "gene(s)," "polynucleotide," "nucleic acid sequence," "nucleotide sequence," "sequence" or "nucleic acid molecule(s)" as used herein refer to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation and "caps" substitution of one or more of the naturally occurring nucleotides with an analog.

"Recombinant nucleic acid molecule" as used herein refers to a polynucleotide of genomic, cDNA, semisynthetic or synthetic origin which, by virtue of its origin or manipulation is:

linked to a polynucleotide other than that to which it is linked in nature, or does not occur in nature.

An "expression vector" is a construct that can be used to transform a selected host cell and provides for expression of a sequence or expression of a gene in the selected host. Expression vectors can, for instance, be cloning vectors, binary vectors or integrating vectors.

"Expression of a sequence" or "expression of a gene" is the transcription of the sequence or gene in RNA and, where applicable, the translation of the coding sequence into protein.

An "expressed sequence" is a nucleotide sequence which is transcribed into mRNA and/or translated into a polypeptide when placed under the control of appropriate regulatory sequences and consists of the sequence between the start of transcription and the stop of transcription. The translated sequence is called coding sequence. The boundaries of the coding sequence are determined by a translation start codon at the 5'-terminus and a translation stop codon at the 3'-terminus. An expressed sequence can include, but is not limited to, mRNA, cDNA, recombinant nucleotide sequences or genomic DNA, while introns may be present as well under certain circumstances.

"Expression of a protein" means the production of a protein or nucleotide sequence in the cell itself or in a cell-free system. It includes transcription into an RNA product, post-transcriptional modification and/or translation to a protein product or polypeptide from a DNA encoding that product, as well as possible post-translational modifications.

"Control sequence" refers to regulatory DNA sequences which are necessary to affect the expression of expressed sequences to which they are ligated and to sequences necessary for the translation of coding sequences. The nature of such control sequences differs depending upon the host organism. In prokaryotes, control sequences generally include a promoter, a ribosomal binding site, and terminators. In eukaryotes, generally, control sequences include promoters, terminators and in, some instances, enhancers, transactivators or transcription factors. The term "control sequence" is intended to include, at a minimum, all components, the presence of which is necessary for expression and translation, and may also include additional advantageous components "Operably linked" refers to a juxtaposition wherein the components so described are in a relationship permitting them to function in their intended manner. A control sequence "operably linked" to an expressed sequence and/or coding sequence is ligated in such a way that expression of the expressed sequence and/or translation of the coding sequence is achieved under conditions compatible with the control sequences. In the case where the control sequence is a promoter, it is obvious for a skilled person that double-stranded nucleic acid is used.

The terms "protein" and "polypeptide" used in this application are interchangeable. "Polypeptide" refers to a polymer of amino acids (amino acid sequence) and does not refer to a specific length of the molecule. Thus, peptides and oligopeptides are included within the definition of polypeptide. The term also refers to or includes post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

"Fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, and preferably a maximum of about 30 amino acids. It is usually desirable to select sequences of at least about 10, 12 or 15 amino acids, up to a maximum of about 20 or 25 amino acids.

"Transformation" as used herein, refers to the transfer of an exogenous polynucleotide into a host cell, irrespective of the method used for the transfer. The polynucleotide may be transiently or stably introduced into the host cell and may be maintained nonintegrated, for example, as a plasmid, or, alternatively, may be integrated into the host genome. Many types of vectors can be used to transform cells. These transformation methods are known to the person skilled in the art.

"Functional part of" means that the part to which subject it relates has substantially the same activity as the subject itself, although the form, length or structure may vary.

The term "substantially homologous" refers to a subject, for instance, a nucleic acid, which is at least 50% identical in sequence to the reference when the entire ORF (open reading frame) is compared, where the sequence identity is preferably at least 70%, more preferably at least 80%, still more preferably at least 85%, especially more preferably more than about 90%, most preferably 95% or greater, and particularly 98% or greater. Thus, for example, a new nucleic acid isolate which is 80% identical to the reference is considered to be substantially homologous to the reference.

Sequences that are substantially homologous can be identified by comparing the sequences using standard software available in sequence data banks, or in a Southern hybridization experiment under, for instance, conventional or preferably stringent conditions as defined for that particular system.

Similarly, in a particular embodiment, two amino acid sequences, when properly aligned in a manner known to a skilled person, are "substantially homologous" when more than 40% of the amino acids are identical or similar, or when, more preferably, more than about 60% and, most preferably, more than 69% of the amino acids are identical or similar (functionally identical).

"Sense strand" refers to the strand of a double-stranded DNA molecule that is homologous to an mRNA transcript thereof. The "anti-sense strand" contains an inverted sequence which is complementary to that of the "sense strand".

"Cell cycle" or "cell division" means the cyclic biochemical and structural events associated with growth and with division of cells and, in particular, with the regulation of the replication of DNA and mitosis. The cycle is divided into periods called: $G_0$, $Gap_1$ ($G_1$), DNA synthesis ("S"), $Gap_2$ ("G2"), and mitosis ("M").

The invention also relates to nucleic acid molecules hybridizing with the above-described nucleic acid molecules and differing in one or more positions in comparison with these as long as they encode a comparable protein. By "hybridizing" is meant that such nucleic acid molecules hybridize under conventional hybridization conditions, preferably under stringent conditions such as described by, e.g., Sambrook (*Molecular Cloning; A Laboratory Manual*, Cold Spring Harbor Laboratory Press, Cold Spring Harbor, N.Y. ($2^{nd}$ ed., 1989)). An example of one such stringent hybridization condition is hybridization at 4×ssC at 65° C., followed by a washing in 0.1×ssC at 65° C. for one hour. Alternatively, an exemplary stringent hybridization condition is in 50% formamide, 4×ssC at 42° C. The invention also relates to nucleic acid molecules, the sequence of which differs from the nucleotide sequence of any of the above-described nucleic acid molecules due to the degeneracy of the genetic code.

"Homology" further means that the respective nucleic acid molecules or encoded proteins are functionally and/or structurally equivalent. The nucleic acid molecules that are homologous to the nucleic acid molecules described above and that are derivatives of the nucleic acid molecules are, for example, variations of the nucleic acid molecules which represent modifications having the same biological function, in particular encoding proteins with the same or substantially the same biological function. They may be naturally occurring variations, such as sequences from other varieties or species, or mutations. These mutations may occur naturally or may be obtained by mutagenesis techniques. The allelic variations may be naturally occurring allelic variants as well as synthetically produced or genetically engineered variants.

The present invention also relates to "vectors", particularly plasmids, cosmids, viruses, bacteriophages and other vectors used conventionally in genetic engineering that contain a nucleic acid molecule according to the invention. Methods which are well known to those skilled in the art can be used to construct various plasmids and vectors; see, for example, the techniques described in Sambrook, Id., and Ausubel, Current Protocols in Molecular Biology (Green Publishing Associates and Wiley Interscience, N.Y. 1989). Alternatively, the nucleic acid molecules and vectors of the invention can be reconstituted into liposomes for delivery to target cells.

The invention is further described and explained by way of the following non-limiting examples. A section disclosing the materials and methods used in the Examples is included also.

EXAMPLES

Example 1

The internal initiation of translation on the PITSLRE p110 (a2-2) mRNA is mediated by an IRES element present in the coding region.

A possible mechanism accounting for the synthesis of p58 is leaky ribosome scanning (Kozak, 1989, 1991). According to this model (proposed by Kozak and coworkers), the small subunit of the ribosome first recognizes the 5' terminal cap structure of an mRNA and then scans the mRNA sequence in a 5' to 3' direction for potential AUG initiation codons. Often, but not always, the first AUG is utilized. Whether this AUG is selected or ignored depends largely on the sequence context surrounding it. An optimal nine nucleotide consensus sequence, 5'-CC(A/G)CCAUGG-3' (SEQ ID NO: 19), has been derived on the basis of extensive mutagenesis experiments (Kozak, 1986). The presence of a purine in position −3 is most important for efficient AUG usage. In the absence of a −3 purine, the presence of a guanosine at position +4 is essential. Ribosomal subunits that fail to initiate at the first AUG can continue their search for an AUG in a more favorable sequence context.

Inspection of the PITSLRE mRNA sequence reveals a poor to moderate match around the first AUG and a very poor match for the nucleotides flanking the AUG of p58 (Table 1). If the scanning mechanism would be used for translational initiation of p58, the ribosomal 43S ternary complex would bind at the 5' end of the mRNA and would scan 1011 nucleotides, bypassing seventeen AUG codons to initiate protein synthesis at the eighteenth AUG codon.

Several of the upstream AUG codons are in a more favorable context to initiate protein synthesis than the eighteenth AUG (Table 1). Because the observations according to the current invention are not compatible with the leaky scanning model, the possibility of the presence of an IRES sequence in the coding region of the PITSLRE mRNA was examined. Bicistronic mRNAs have been effectively used in vivo to demonstrate the existence of IRES sequences in both viral and cellular mRNAs. A plasmid vector in which the SV40 promoter drives the transcription of a capped bicistronic transcript was constructed in the present invention (FIG. 4A). The first cistron, encoding luciferase (LUC) should be translated by the conventional cap-dependent scanning mechanism. However, as ribosomes fail to continue scanning through the intercistronic spacer (ICS) insert, the second cistron, encoding b-galactosidase (LACZ), should be translated only if the preceding sequence contains an IRES.

The region starting from position 121 was first subcloned and ended up at the internal initiation codon ATG (p58) (position 1126) by PCR amplification (Di-1, FIG. 4A), and the plasmid was transient transfected into the 293 T cell line. The translation products were monitored in enzymatic assays (FIG. 4B) and by western blotting (FIG. 4C). As expected, the dicistronic mRNA produced luciferase. Interestingly, the same lysate was also positive in the LACZ activity test. Western blot analysis showed that both translation products were of the correct size, excluding the occurrence of fusion proteins (FIG. 4C). The observation that LACZ is translated from the dicistronic transcript suggests the presence of an internal ribosomal entry site in the ICS.

To exclude the possibility that the function of the potential IRES-element is to promote the transfer of initiation-competent ribosomes from the termination codon of the upstream cistron to the initiation codon of the downstream cistron, a hairpin near the 5' end was inserted (HPDi-1). FIG. 4D shows that this modification only negatively influences translation of the first cistron while LACZ expression remains unaffected. If enhanced ribosomal read through is responsible for the ICS-responsible stimulation of LACZ, then this activity should be reduced by an equivalent amount.

In addition, two constructs were made in which the p58 coding region in p110 PITSLRE in frame was exchanged by the coding region of luciferase. In one of them, a frame shift was induced in the PITSLRE-specific region by deleting two nucleotides (926/927). Both cDNAs were transiently transfected into 293T cells. The respective translation products of the in-frame fusion mRNA and the frame shift fusion mRNA were analyzed by immunoblotting with anti-LUC antibody. In accordance with p110$^{PITSLRE}$, in the cell lysates of the in-frame fusion mRNA, two translation products were detected: a fusion product of 130 kDa (p110-LUC) and luciferase. In the cell lysates of the frame shift fusion mRNA, only one translation product, luciferase, was detected. The frame shift abrogated the translation of the fusion protein of 130 kDa, while internal translation of luciferase conferred by the PITSLRE IRES element remained unaffected.

To exclude the possibility that LACZ was expressed from a monocistronic mRNA that might have been generated if the IRES element had sites for cleavage by a specific ribonuclease or if the IRES had a cryptic promoter element, Northern blot analysis was performed. The same mRNA was detected both by luciferase and LACZ probes. This observation demonstrated that both cistrons were translated from an intact dicistronic form of the mRNA (FIG. 4E).

Figure 5:
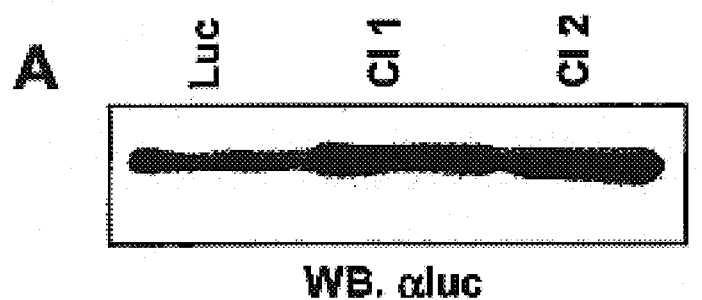
Figure 5:
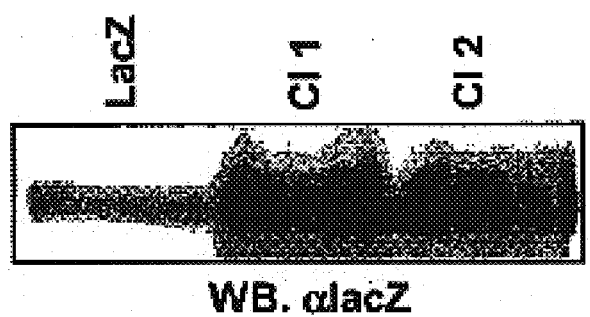
Figure 5:
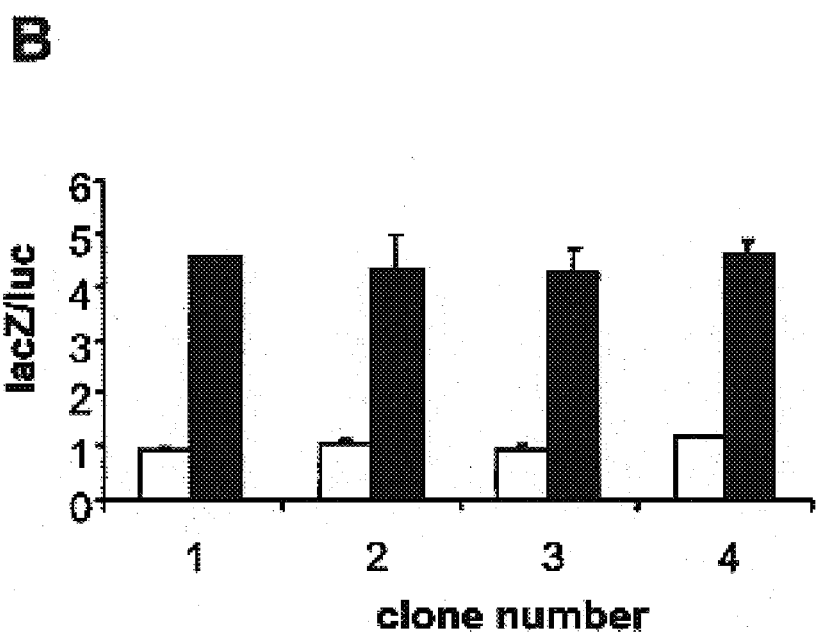

To determine whether the cellular environment in the G2/M stage of the cell cycle is more supportive for internal initiation of translation mediated by the PITSLRE IRES element, the dicistronic vector was stably transfected into the Ba/F3 cell line. Several clones were obtained and analyzed during cell cycle progression (FIG. 5). Luciferase and LACZ activity were determined in cell lysates prepared at different time points during cell cycle progression. The G2/M stage is associated with enhanced LACZ activity, corrected for the amount of mRNA by measurement of luciferase activity (FIG. 5B). A 3–5 times enhanced LACZ/LUC ratio was measured in the G2/M stage compared to the G1 stage. Hence, it seems that the G2/M-stage facilitates the internal initiation.

The fact that LACZ activity can still be detected at the G1 stage of the cell cycle might be a consequence of the higher stability of the protein compared to the stability of p58 (FIG. 5A).

TABLE 1

| N°AUG | AUG position | AUG context (CC(A/G)CCAUGG (SEQ ID NO: 19) |
|---|---|---|
| 1 | 112 (p110) | CUCAAAUGG (SEQ ID NO: 20) |
| 2 | 119 | GGGUGAUGA (SEQ ID NO: 21) |
| 3 | 152 | UUUAGAUGA (SEQ ID NO: 22) |
| 4 | 227 | UUCUGAUGA (SEQ ID NO: 23) |
| 5 | 283* (p105) | ACUGCAUGG (SEQ ID NO: 24) |
| 6 | 328* | ACUCUAUGG (SEQ ID NO: 25) |
| 7 | 350 | AGAAGAUGA (SEQ ID NO: 26) |
| 8 | 382* | AGCAAAUGU (SEQ ID NO: 27) |
| 9 | 416 | AAAAGAUGA (SEQ ID NO: 28) |
| 10 | 440 | AAAGCAUGC (SEQ ID NO: 29) |
| 11 | 519 | CGGGAAUGG (SEQ ID NO: 30) |
| 12 | 544* | GGGAAAUGG (SEQ ID NO: 31) |
| 13 | 578 | GGGGAAUGA (SEQ ID NO: 32) |
| 14 | 581 | GAAUGAUGG (SEQ ID NO: 33) |
| 15 | 646* | GCAAGAUGC (SEQ ID NO: 34) |
| 16 | 757* | GAACGAUGA (SEQ ID NO: 35) |
| 17 | 874* | AGAAAAUGG (SEQ ID NO: 36) |
| 18 | 1126* (p58) | AAGAAAUGA (SEQ ID NO: 37) |

*: in frame AUG
in bold: matches with consensus sequence according to Kozak, 1986.

Example 2

Characterization of the PITSLRE IRES Element

The cloned fragment in the ICS in the dicistronic vector, Di-1, contains 1005 nucleotides. Regions described to contain IRES activity are maximally 450 bp long. To map the region with IRES activity in the PITSLRE mRNA, a series of dicistronic plasmids was generated containing decreasing lengths of sequence coding for p110$^{PITSLRE}$. Different fragments (FIG. 4) were inserted into the intercistronic spacer region (Di 2 to Di 6) and transient transfected dicistronic plasmids were introduced into the 293T cell line. As expected, all dicistronic mRNAs produced luciferase. The luciferase activity was used as an internal control for the different transaction efficiencies of the plasmids.

The ability of the truncated sequences to promote internal ribosomal entry on the dicistronic mRNA was compared to Di-1.

The constructs containing fragments of the 5' end of the analyzed region did not score in the LACZ activity test (FIG. 4B, Di-2, Di-3). Extended deletions at the 3' end completely abrogated internal initiation, suggesting that the IRES element is situated upstream of the internal initiation codon.

Interestingly, deletion of 347 nucleotides at the 5' end had little effect on the activity of the downstream cistron (Di-4) although it resulted in a LACZ product that is slightly bigger (FIG. 4C). Larger deletions of 624 nucleotides (D-5) and 786 nucleotides (Di-6) resulted in a corresponding reduction of internal ribosome entry of 25% and 50%, respectively. This partial loss of IRES activity may reflect loss of secondary or tertiary structure elements that confer positive or negative effects or loss of protein-binding sites. The IRES activity harbored in the ICS of Di-4 is comparable in strength with the activity in the ICS of Di-1. The fact that it is possible to make a small deletion at the 3' end without a dramatic loss of activity has also been described for the c-myc IRES (Stoneley et al., 1998).

Analysis of the translation products from the different dicistronic mRNAs by Western blot analysis, shown in FIG. 4C, shows that Di-1, Di-5 and Di-6 express LACZ of the expected size. Di-4, which also scored positive in the LACZ activity test, expresses a larger LACZ specific translation product. It seems that deletion of a small region immediately upstream of the AUG of internal initiation of translation does not interfere with activity, in casu ribosome binding, but affects the site of initiation of translation taken by the ribosomes. In various viral IRESs 3' end deletions located within the IRES completely ablate ribosomal entry.

The PITSLRE IRES element contains a purine-rich tract (93% A/G) of 90 nucleotides, which is situated 60 nucleotides upstream of the AUG (p58). A similar polypurine motif has also been found in a tobamoviral IRES (Ivanov et al., 1997). The functional significance of this motif is still unclear. Possibly, it plays a functional role in analogy with the oligopyrimidine motif that has been described for the picomavirus IRES (Pilipenko et al., 1992; Jackson et al., 1994).

The cloned fragment in the ICS in the dicistronic vector, Dppt, is similar to the corresponding region in Di-1, but contains a deletion of the purine-rich tract starting at position 978 and ending up at position 1065.

In FIG. 4B, we show that this deletion ablates DES-mediated internal initiation.

Example 3
Structural Features of the PITSLRE IRES Element

The importance of RNA secondary and tertiary structure for IRES function emerges from a comparison of the sequences and secondary structures of different IRESs. A common RNA structural motif involved in the internal initiation of cellular mRNAs has been proposed by Le and coworkers (Le and Maizel, 1997). A common RNA structural motif, including a Y-type stem-loop followed by a stem-loop, is a conserved property found in cellular IRES elements. One remarkable property of the stem-loop is that this structure is situated just upstream from the authentic initiator (Le and Maizel, 1997). The secondary structure of a fragment of 491 bp (nucleotides 637 to 1128) of the p110$^{PITSLRE}$ mRNA is shown to contain IRES activity. This secondary structure is predicted by the Zuker procedure (computer program: mfold).

Two structural domains seem to correlate with IRES activity: a Y-type stem-loop (689–823) and stem-loop (1069–1105). D G=−128.2 kcal/mol.

Material and Methods
Plasmid Constructions

The p110$^{PITSLRE}$ cDNA was obtained by reverse transcription and polymerase chain reaction (PCR) amplification of total mRNA from human HL-60 cells using Superscript reverse transcriptase (Life Technologies, Inc.) and High Fidelity DNA polymerase (Boehringer). The 5'- and 3'-primers used for this amplification, 5'-TGACCGGAATTCA TGGGTGATGAAAAGGACCTTTGG-3' (SEQ ID NO: 38) and 5'-TGACCGGAATTCTGACCTTCAGAACTTGA GGCTGAAGCC-3' (SEQ ID NO: 39), respectively, gave a cDNA fragment of 2400 bp. The PCR fragment was digested with the restriction enzyme EcoRI and cloned into the pMA58 plasmid. This construction was used to perform site-directed mutagenesis by a chloramphenicol-selection procedure using a commercially available kit (Transformer, Clonetech). Briefly, this method involves simultaneously annealing of two oligonucleotide primers to one strand of the denatured double-stranded plasmid (pMA-p110$^{PITSLRE}$). One primer introduces the desired mutation. The second primer induces a gain of function mutation in the gene encoding chloramphenicol resistance for the purpose of selection.

To fuse an E-tag at the 3'-end of p110$^{PITSLRE}$ cDNA, an in-frame NotI restriction site was introduced at the stop codon by using the mutation primer 5'-AGCCTCAAGTT CGCGGCCGCAGAGTGGACC-3' (SEQ ID NO:8). As an EcoRI/NotI fragment, the p110$^{PITSLRE}$ cDNA was inserted in the EcoRI/NotI opened pSV-Sport-E-tag plasmid. The latter was obtained by insertion of the E-tag as a NotI/XbaI fragment in the NotI/XbaI opened pSV-Sport plasmid.

The following primers were used for the mutation of the internal initiation codon and for the induction of the frame shift, respectively: 5'-GAGGAAGAAGCGAGTGAAGAT-3' (SEQ D NO: 9) and 5'-GACAGCGAGAAAGACCA GCTCG-3' (SEQ ID NO: 10).

The dicistronic vectors were made by first cloning the PCR fragments and LACZ gene into the pUC19 plasmid performed by a three points ligation. In a subsequent three points ligation, the PCR fragment fused to the LACZ gene was inserted together with the firefly luciferase gene into the pSV-Sport plasmid.

The 5'-end and 3'-end primers used for amplification of the different fragments cloned into the intercistronic spacers of the different dicistronic vectors are: Di-1: sense: 5'-CTA GTCTAGAAAAGTGAAAACTTTAGATGAAATTC-3' (SEQ ID NO: 11); antisense: 5'-TTCTTCATCTTCACCCA TGGCTTCCTCACTTAC-3' (SEQ ID NO:40); Di-2: sense: idem Di-1; antisense: 5'-TGCATGCCATGGTCCTCTCTC ATCGTTCGGTGATG-3' (SEQ ID NO: 13); Di-3: sense: idem Di-1; antisense: 5'-TGCATGCCATGGATGTCGTTT CCGACGTTCGTGCG-3' (SEQ ID NO: 12); Di-4: sense: 5'-CTAGTCTAGAGCACGAACGTCGGAAACGACAG-3' (SEQ ID NO: 41); antisense: 5'-CATGCCATGGTC TTCCTCTCGCTGTCGCTGATGTC-3' (SEQ ID NO: 14); Di-5: sense: 5'-CTAGTCTAGACATCACCGAACGATG AGAGAGG-3' (SEQ ID NO: 21); antisense: idem Di-1; Di-6 sense: 5'-CTAGTCTAGAGACATCAGCGACAGC GAGAGGAAGACCAGC-3' (SEQ ID NO: 42); antisense: idem Di-1. The PITSLRE-specific ICS in Dppt was obtained by PCR amplification. Two fragments were amplified with the following primers: 5'-CTAGTCTAGAAAAGTGA AAACTTTAGATGAAATTC-3' (SEQ ID NO: 11), 5'-CCATCGATAGAACCTGAGCCTGATTCTGCTGAC GA-3' (SEQ ID NO: 43) and 5'-CCATCGATACCG GCAGCAACTCTGAGGAGGCATC-3' (SEQ ID NO: 44); 5'-TTCTTCATCTTCACCCATGGCTTCCTCACTTAC-3' (SEQ ID NO: 45).

The subsequent PCR fragments were digested with the restriction enzymes: XbaI and NcoI. These fragments were cloned together with a LACZ gene as a NcoI/SalI fragment (from pIRES-LACZ) in an XbaI/SalI-opened pUC19 plasmid. For the Dppt, the fragments obtained were digested with XbaI/ClaI and ClaI/NcoI, respectively, and ligated with a NcoI/SalI LACZ-containing fragment in XbaI/SalI-opened pUC19. Subsequently, the complete insert was cloned as an XbaI/SalI fragment in the KpnI/SalI-opened pSV-Sport plasmid together with the firefly luciferase gene that was cloned as a KpnI/XbaI fragment (from the pGL3-basic vector (Clonetech).

A stable hairpin (D G=−40 kcal/mol) was created by introduction of a double-stranded oligonucleotide (5'-CGCGTGGCGAGATTTTCAGGAGTCAC-3' (SEQ ID NO: 16) and 5'-TCGAGTGACTCCTGAAAATCTCGCCA-3' (SEQ ID NO: 17)) between the MluI and XhoI sites of vector pGL3-basic upstream of the luciferase gene. This was accomplished by ligation of the double-stranded oligonucleotide (with MluI and XhoI ends) with the MluI/XhoI-opened pGL3-basic vector.

Cells and DNA Transfection

Human embryonic kidney 293T cells were maintained in Dulbecco's modified Eagle's medium ("DMEM") supplemented with 10% (v/v)heat inactivated FCS.

The IL-3-dependent mouse pro-B cell line Ba/F3 (Palacios and Steinmetz, 1985) was maintained in DMEM supplemented with 10% (v/v) heat inactivated FCS and 20% (v/v) conditioned medium from the WEHI-3B cells as a source of mIL-3.

293T cells were transiently transfected by a calcium phosphate precipitation method (O'Makoney and Adams, 1994). Cells were incubated for at least 4 h with the transfection solution followed by adding fresh medium. Cells were collected by centrifugation at 48 h post-transfection and were further analyzed.

Ba/F3 cells were stably transfected by electroporation. Before transfection, cells were collected and resuspended at $1\times10^7$ cells per ml in medium. 20 mg of p110$^{PITSLRE}$ plasmid and 5 mg of carrying a puromycine resistance gene (pBSpacdeltap) (De la Luna, S. et al., 1988) was added to 0.8 ml of cell suspension. Electroporation was performed using the Easy Ject apparatus (Eurogentec) at 1500 mF and 300 V. Subsequently, the cells were resuspended in WEHI-3B supernatant-supplemented growth medium. Selection was initiated 48 h after transfection in medium containing 1 mg/ml puromucin (Sigma). After one week, surviving cells were cloned by limiting dilution. Positive transfectants were selected on the basis of immunoblotting or reporter gene expression measured by enzymatic assays.

WESTERN BLOT ANALYSIS—For Western blot analysis, cells were lysed in a 1% NP40 lyse buffer (20 mM Tris-HCl pH 8.0, 137 mM NaCl, 10% glycerol, 1 mM Pefablock (Merck), 200 u/ml aprotinin, 10 mM EDTA, 10 mg/ml leupeptin).

Total proteins were quantified in the precleared cell lysates by the Biorad assay (A295) and 50 mg of proteins were subjected to SDS-PAGE and transferred by electroblotting onto a nitrocellulose membrane. E-tag fused proteins were immunodetected with the mouse monoclonal anti-E-tag antibody (1/1000 dilution) (Pharmacia). LACZ and firefly luciferase were immunodetected with the mouse monoclonal anti LACZ (1/1000 dilution) (Boehringer) and rabbit polyclonal anti-luciferase antibody (1/2000 dilution) (Promega), respectively.

PITSLRE protein kinases and Cyclin B1 were immunodetected by the rabbit polyclonal anti PITSLRE antibody (1/1000) (Santa Cruz) and the rabbit polyclonal anti cyclin B1 antibody (dilution 1/1000) (Santa Cruz), respectively.

Antibodies were detected with an enhance chemiluminescence kit (Amersham).

REPORTER GENE ASSAYS—For the reporter gene assays, cells were lysed in 25 mM tris phosphate pH 8,2 mM DTT, 2 mM CDTA, 10% glycerol, 1% triton X-100.

Firefly luciferase was assayed in a volume of 30 ml. The reactions were initiated by addition of 15 ml of luciferase assay/substrate buffer (40 mM Tricine, 2 mM $(MgCO_3)4Mg(OH)_2.H_2O$, 5 mM $MgSO_4$, 66 mM DTT, 0.2 mM EDTA, 0.5 mM CoA, 1 mM ATP, 1 mM D-luciferin) to 15 ml cell lysate. The light signal was measured using a Top-Count (Packard).

b-galactosidase was measured in a volume of 200 ml. Twenty ml lysate was added to 160 ml substrate buffer (60 mM $Na_2HPO_4$, 10 mM KCl, 1 mM b-ME) and reaction was initiated by adding 20 ml of 50 mM chlorophenolred-b-D galactopyranoside (CPRG). The colorimetric signal was measured at 595 nm.

CELLULAR RNA PURIFICATION AND NORTHERN BLOTTING—Total RNA was isolated making use of the RNAeasy™ kit (Quiagen) according to the manufacturer's instructions.

Total cellular RNA (10 mg/lane) was denatured in formaldehyde and electrophoresed through a 1.2% formaldehyde-agarose gel. RNAs were transferred onto a nylon membrane (Amersham) by the capillary blot procedure. The filters were UV cross-linked using a UV Stratalinker apparatus (Stratagene) and were hybridized with the indicated cDNAs labeled with $^{32}$P by randomly primed DNA synthesis. The hybridization probes were luciferase (a 1700 bp cDNA NcoI/XbaI restriction fragment), LACZ (a 800 bp cDNA NcoI/ClaI restriction fragment), PITSLRE (a 650 bp PvuII restriction fragment) and an E-tag probe (5'-ACGCGGTTCCAGCGGATCCGGATACGGCTCCGGCGCACCT-3' (SEQ ID NO: 18)).

REFERENCES

Beyaert, R., Kidd, V. J., Cornelis, S., Van de Craen, M., Denecker, G., Lahti, J. M., Gururajan, R., Vandenabeele, P. and Fiers, W. (1997). Cleavage of PITSLRE kinases by ICE/CASP-1 and CPP32/CASP-3 during apoptosis induced by tumour necrosis factor. *J. Biol. Chem.* 272, 11694–11697.

Bunnell, B. A., Heath, L. S., Adams, D. E., Lahti, J. M. and Kidd, V. J. (1990). Increased expression of a 58-kDa protein kinase leads to changes in the CHO cell cycle. *Proc. Natl. Acad. USA*, 87, 7467–7471.

De la Luna, S., Inmaculada, S., Pulido, D., Ortin, J., and Jimenez, A. (1988). Efficient transformation of mammalian cells with constructs containing a puromycin-resistance marker. *Gene* 62, 121.

Eipers, P. G., Barnoski, B. L., Han, J., Caroll, A. J. and Kidd, V. J. (1991). Localization of the expressed p58 protein kinase chromosomal gene to chromosome 1p36 and a highly related sequence to chromosome 15. *Genomics* 11, 621–629.

Gerard, R. D., Collen, D. (1997). Adenovirus gene therapy for hypercholesterolemia, thrombosis and restenosis. *Cardiovasc. Res.* 35:451–8.

Ivanov, P. A., Karpova, O. V., Skulachev, M. V., Tomashevskaya, O. L., Rodionova, N. P., Dorokhov, Y. L. and Atabekov, J. G. (1997). A tobamovirus genome that contains an internal ribosome entry site functional in vitro. *Virology* 232, 32–43.

Jang, S. K., Krausslich, H. G., Nicklin, M. J., Duke, G. M., Palmenberg, A. C., Wimmer, E. (1988). A segment of the 5' nontranslated region of encephalomyocarditis virus RNA directs internal entry of ribosomes during in vitro translation. *J. Virol.* 62(8):2636–43.

Jackson, R. J., Hunt, S. L., Gibbs, C. L. and Karninski, A. (1994). Internal initiation of picornavirus RNAs. *Mol. Biol. Rep.* 19, 147–159.

Kozak, M. (1986). Point mutations define a sequence flanking the AUG initiator codon that modulates translation by eukaryotic ribosomes. *Cell* 44, 283–292.

Kozak, M., (1989). The scanning model for translation: An update. *J. Cell. Biol.* 108, 229–241.

Kozak, M. (1991). An analysis of vertebrate mRNA sequences: Intimations of translational control. *J. Cell. Biol.* 115, 887–903.

Lahti, J. M., Valentine, M., Xiang, J., Jones, B., Amann, J., Grenet, J., Richmond, A., Look, T. and Kidd, V. J. (1994). Alterations in the PITSLRE protein kinase gene complex on chromosome 1p36 in childhood neuroblastoma. *Nat. Genet.* 7, 370–375.

Lahti, J. M., Xiang, J., Heath, L. S., Campana, D. and Kidd, V. J. (1995). PITSLRE protein kinase activity is associated with apoptosis. *Mol. Cell. Bol.* 15, 1–11.

Le, S-Y and Maizel, J. V. (1997). A common RNA structural motif involved in the internal initiation of translation of cellular mRNAs. *NAR*, 25, 362–369.

Loyer, P., Trembley, J., Lahti, J. M. and Kidd, V. J. (1998). The RNP protein, RNPS1, associates with specific isoforms of the p34cdc2-related PITSLRE protein kinase in vivo. *J. Cell Science* 111, 1495–1506.

Meyerson, M. A family of human cdc2-related kinases *EMBO J.*, 11, 2909–2917.

Molla, A., Paul, A. V. and Wimmer, E. (1991). Cell-free, de novo synthesis of poliovirus. *Science*, 254, 1647–1655.

O'Mahoney, J. V. and Adams, T. E. (1994). Optimization of experimental variables influencing receptor gene expression in hepatoma cells following calcium phosphate transfection. *DNA Cell Biol.* 13, 1227–1232.

Palacios, R., and Steinmetz, M. (1985). IL3-dependent mouse clones that express B-220 surface antigen contain Ig genes in germ-line configuration, and generate B lymphocytes in vivo. *Cell 41*, 727.

Pilipenko, E. V., Gmyl, A. P., Maslova, S. V., Svitkin, Y. V., Sinyakov, A. N. and Agol, V. I. (1992). Prokaryotic-like cis-elements in the cap-independent internal initiation of translation on picornavirus RNA. *Cell* 68, 119–131.

Sauer, K., Weigmann, K., Sigrist, S. and Lehner, C. F. (1996). Novel members of the cdc2-related kinase family in Drosophila: cdk4/6, cdk5, PFTAIRE and PITSLRE kinases. *Mol. Biol. Cell*, 7, 1759–1769.

Schwartz, R. S., Holmes, D. R. Jr., Topol, E. J. (1998). The restenosis paradigm revisited: an alternative proposal for cellular mechanisms. *J. Am. Coll. Cardiol.* 20: 1284–93.

Stoneley, M. F., Paulin, F. E., Le Quesne, J. P., Chappell, S. A., and Willis, A. E. (1998). C-Myc 5' untranslated region contains an internal ribosome entry segment. *Oncogene* 16, 423–428.

Tang, D., Gururajan, R., and Kidd, V. J. (1998). Phosphorylation of PITSLRE p110 isoforms accompanies their processing by caspases during Fas-mediated cell-death. *J. Biol. Chem.* 273, 16601–16607.

Tio, R. A., Isner, J. M., Walsh, K. (1998). Gene therapy to prevent restenosis, the Boston experience. *Semin. Interv. Cardiol.* 3:205–10.

Varenne, O., Gerard, R. D., Sinnaeve, P., Gillijns, H., Collen, D., Janssens, S. (1999) Percutaneous adenoviral gene transfer into porcine coronary arteries: is catheter-based gene delivery adapted to coronary circulation? *Hum. Gene Ther.* 10:1105–15.

Xiang, J., Lahti, J. M., Grenet, J., Easton, J. and Kidd, V. J. (1994). Molecular cloning and expression of alternative spliced PITSLRE protein kinase isoforms. *J. Biol. Chem.* 269, 15786–15794.

---

What is claimed is:

1. A nucleic acid molecule consisting of a nucleic acid sequence selected from the group consisting of SEQ ID NO:1, SEQ ID NO:7, and combinations thereof.

2. A recombinant nucleic acid molecule consisting of SEQ ID NO:1, 4–6 or 7.

3. A chimeric gene comprising:
   (a) said recombinant nucleic acid molecule of claim 2, and
   (b) one or more control sequences operably linked to said recombinant nucleic acid molecule.

4. A vector comprising the recombinant nucleic acid molecule of claim 2.

5. The vector of claim 4 wherein said vector is an expression vector, said vector further comprising a promoter.

6. An isolated eukaryotic host cell comprising the recombinant nucleic acid molecule of claim 2.

7. An expression system comprising the isolated eukaryotic host cell of claim 6.

8. A vector comprising the chimeric gene of claim 3.

9. An isolated eukaryotic host cell comprising the chimeric gene of claim 3.

10. A nucleic acid molecule consisting of a nucleic acid sequence selected from the group consisting of SEQ ID NO:4, SEQ ID NO:5, SEQ ID NO:6 and combinations thereof, said nucleic acid sequence initiating the translation of mRNA in a eukaryotic cell.

11. A chimeric gene comprising:
   a) the nucleic acid molecule of claim 10, and
   b) one or more control sequences operably linked to said nucleic acid molecule.

12. A vector comprising the nucleic acid molecule of claim 10.

13. The vector of claim 12 wherein said vector is an expression vector, said vector further comprising a promoter.

14. An isolated eukaryotic host cell comprising the nucleic acid molecule of claim 10.

15. An expression system comprising the isolated eukaryotic host cell of claim 14.

16. A vector comprising the chimeric gene of claim 11.

17. The vector of claim 16, wherein said vector is an expression vector, said vector further comprising a promoter.

18. An isolated eukaryotic host cell comprising the chimeric gene of claim 11.

19. An expression system comprising the isolated eukaryotic host cell of claim 18.

20. An expression system comprising the isolated eukaryotic host cell of claim 9.

21. The recombinant nucleic acid molecule of claim 2, wherein said recombinant nucleic acid molecule enables a G2/M cell cycle-dependent initiation of translation of mRNA.

22. The recombinant nucleic acid molecule of claim 21, wherein said recombinant nucleic acid molecule is an internal ribosomal entry site sequence which initiates mRNA translation in a eukaryotic cell.

23. The nucleic acid molecule of claim 1, wherein said nucleic acid sequence is a eukaryotic internal ribosomal entry site which initiates mRNA translation in a eukaryotic cell.

* * * * *

UNITED STATES PATENT AND TRADEMARK OFFICE
CERTIFICATE OF CORRECTION

PATENT NO. : 6,764,852 B2  Page 1 of 1
APPLICATION NO. : 09/915060
DATED : July 20, 2004
INVENTOR(S) : Sigrid Cornelis and Rudi Beyaert It is certified that error appears in the above-identified patent and that said Letters Patent is hereby corrected as shown below:

On the title page:
In ITEM (56) References Cited, "Other Publications," 2nd column, 12th line, in Bag et al., after "Rat Muscle Cells", delete "ENDFIELD"

In the specification:

| | | |
|---|---|---|
| COLUMN 4, | LINE 43, | change "capase-processed" to --caspase-processed-- |
| COLUMN 6, | LINES 60-61, | change "thyrnidine kinase" to --thymidine kinase-- |
| COLUMN 7, | LINE 7, | change "forcoronary arterydisease" to --for coronary artery disease-- |
| COLUMN 7, | LINES 33-34, | change "orderivatives thereof." to --or derivatives thereof.-- |
| COLUMN 13, | LINES 35-36, | change "DES-mediated" to --IRES-mediated-- |
| COLUMN 16, | LINE 62, | change "Karninski, A." to --Kaminski, A.-- |

Signed and Sealed this

Twentieth Day of May, 2008

JON W. DUDAS
*Director of the United States Patent and Trademark Office*